United States Patent
Ichikawa et al.

(10) Patent No.: US 6,255,321 B1
(45) Date of Patent: Jul. 3, 2001

(54) 2-SULFAMOYLBENZOIC ACID DERIVATIVES

(75) Inventors: Yoshihiro Ichikawa, Shizuoka; Tokiko Nishida; Jun Nakano, both of Kyoto; Mitsuru Watanuki, Tokyo; Masahiro Suda; Tsutomu Nakamura, both of Kyoto, all of (JP)

(73) Assignee: Kaken Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/445,976

(22) PCT Filed: Jun. 12, 1998

(86) PCT No.: PCT/JP98/02585

§ 371 Date: Dec. 15, 1999

§ 102(e) Date: Dec. 15, 1999

(87) PCT Pub. No.: WO98/57935

PCT Pub. Date: Dec. 23, 1998

(30) Foreign Application Priority Data

Jun. 17, 1997 (JP) ................................................. 9-176458

(51) Int. Cl.[7] .................. A61K 31/428; A61K 31/4709; C07D 215/36; C07D 277/26; C07D 277/80
(52) U.S. Cl. .......................... 514/311; 514/365; 546/172; 546/180; 548/203; 548/205
(58) Field of Search ..................................... 514/311, 365; 548/203, 205; 546/172, 180

(56) References Cited

U.S. PATENT DOCUMENTS

| | | | |
|---|---|---|---|
| 4,876,346 | * | 10/1989 | Musser et al. . |
| 4,902,700 | | 2/1990 | Hayasi et al. . |
| 5,110,819 | | 5/1992 | Ahnfelt-Ronne et al. . |
| 5,981,559 | | 11/1999 | Nagaoka et al. . |

FOREIGN PATENT DOCUMENTS

| | | | |
|---|---|---|---|
| 62-142168 | * | 10/1985 | (JP) . |
| 3-501477 | * | 11/1988 | (JP) . |
| 96-11916 | * | 4/1996 | (WO) . |

* cited by examiner

Primary Examiner—Taofiq A. Solola
(74) Attorney, Agent, or Firm—Nixon Peabody LLP

(57) ABSTRACT

2-Sulfamoylbenzoic acid derivatives of general formula (I):

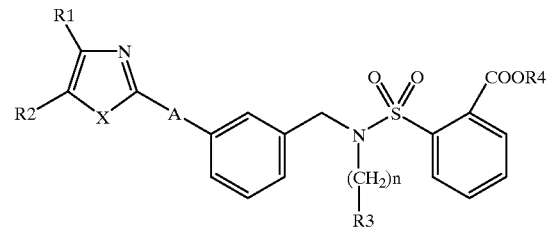

which have both an antagonistic effect on the leukotriene $D_4$ receptor and an antagonistic effect on the thromboxane $A_2$ receptor and salts thereof, pharmaceuticals, anti-allergic agents and leukotrienethromboxane $A_2$ antagonistic agents containing them as an active ingredient.

15 Claims, No Drawings

2-SULFAMOYLBENZOIC ACID DERIVATIVES

DESCRIPTION

This application is a 371 of PCT/JP98/02585 filed Jun. 12, 1998.

TECHNICAL FIELD

The present invention relates to novel 2-sulfamoylbenzoic acid derivatives which have an antagonistic effect on both the leukotriene $D_4$ (hereinafter referred to simply as $LTD_4$) receptor and the thromboxane $A_2$ (hereinafter referred to simply as $TXA_2$) receptor, intermediates for their synthesis and their salts and medicines containing them.

BACKGROUND ART

For treatment of allergic diseases including bronchial asthma, anti-allergic agents such as histamine receptor antagonists and mediator release suppressants for mast cells and steroid drugs have been used, and for bronchial asthma, bronchodilators such as xanthine derivatives and stimulators for the β-sympathetic nerve receptor have been used as well.

In recent years, allergic diseases are recognized as allergic inflammations by their pathological profiles and have been found to be associated with various inflammatory cells and mediators. For example, bronchial asthma is characterized by increased sensitivity of the respiratory tract to various stimuli and defined as involving reversible stenosis of the respiratory tract, mucosal edema of the respiratory tract, mucous supersecretion and infiltration of inflammatory cells onto the walls of the respiratory tract.

Further, with respect to the related mediators, it is suggested that $LTD_4$ not only has an intense bronchoconstrictor effect but also enhances the permeability of the respiratory tract vessels and mucus secretion, and that $TXA_2$ not only has a potent bronchoconstrictor effect but also controls the sensitivity of the respiratory tract.

With the above-mentioned movements in research on treatment of allergic diseases, $LTD_4$ receptor antagonists, $TXA_2$ synthesis inhibitors and $TXA_2$ receptor antagonists have been marketed and shown to be more effective than conventional anti-allergic agents.

However, because development of allergic diseases represented by bronchial asthma pathologically involves various mediators in parallel as mentioned above, antagonism against a receptor for a single mediator or inhibition of synthesis of a single mediator has its limit in terms of effect, and development of novel promising anti-allergic agents which show greater therapeutic effects by inhibiting both $LTD_4$ and $TXA_2$, major pathological mediators in allergy.

Compounds which have antagonistic effects on the receptors for both of the two mediators, $LTD_4$ and $TXA_2$, are disclosed in JP-A-3-258759, JP-A-4-154757, JP-A-4-154766, JP-A-5-262736, JP-A-5-279336, JP-A-6-41051 and WO96/11916. These compound are structurally different from the compounds of the present invention and are not expected to have satisfactory therapeutic effects as anti-allergic agents in view of the intensities of their antagonistic effects on the receptors for the major bronchoconstricting mediator $LTD_4$ and the ratios of their antagonistic activities against the two mediators $LTD_4$ and $TXA_2$.

The present invention has been accomplished in view of the current situations in treatment of allergic diseases and research on their treatment with the aim of providing novel compounds which show potent antagonistic effects on the receptors for $LTD_4$ and $TXA_2$, which are the two major mediators in development of allergic diseases, and therefore are expected to have more excellent therapeutic effects and pharmaceuticals containing them as active ingredients.

DISCLOSURE OF THE INVENTION

In the above-mentioned movements in treatment of allergic diseases and research on their treatment, the present inventors have conducted extensive research with a view to attaining the above-mentioned object and, as a result, found out that the 2-sulfamoylbenzoic acid derivatives of the present invention have antagonistic effects on the receptors for the two mediators $LTD_4$ and $TXA_2$, which play important roles in development of allergic diseases, and have more excellent therapeutic effects than the above-mentioned receptor antagonists against a single mediator and inhibitors against synthesis of a single mediator. The present inventors have accomplished the present invention on the basis of this discovery.

Namely, the present invention provides 2-sulfamoylbenzoic acid derivatives represented by general formula (I):

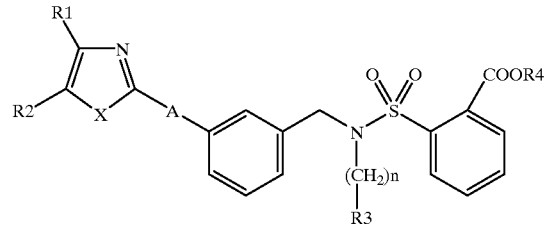

(wherein R1 and R2 which may be the same or different, are hydrogen atoms, $C_{3-8}$ cycloalkyl groups, optionally substituted $C_{1-6}$ alkyl groups, optionally substituted aryl groups or form, together with the ring

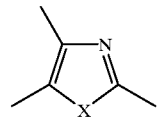

a condensed ring represented by formula

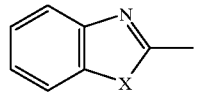

which may be substituted with an optionally substituted $C_{1-6}$ alkyl group, an amino group, a cyano group, a nitro group, a hydroxyl group, a halogen atom or a $C_{1-5}$ alkoxy group, X is an oxygen atom, a nitrogen atom, a sulfur atom or —CH═CH—, R3 is an optionally substituted phenylsulfonylamino group, an optionally substituted phenylsulfonyl group or an optionally substituted phenylsulfoxide group, R4 is a hydrogen atom or an ester residue, n is an integer of from 2 to 6, A is —O—B—, —B—O—, —S—B—, —B—S— or —B—, and B is a $C_{1-6}$ alkylene group or a $C_{2-5}$ alkenylene group, provided that the cases wherein R1 is a $C_{1-6}$ alkyl group, a $C_{3-8}$ cycloalkyl group or a phenyl group, R2 is a hydrogen atom, A is a vinylene group, and X is a sulfur atom are excluded) or salts, hydrates or solvates thereof.

The present invention also provides, as useful intermediates for their synthesis, benzylamine derivatives represented by general formula (II):

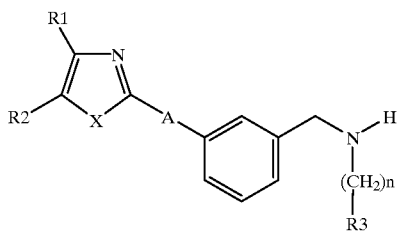

(wherein R1 and R2 which may be the same or different, are hydrogen atoms, $C_{3-8}$ cycloalkyl groups, optionally substituted $C_{1-6}$ alkyl groups, optionally substituted aryl groups or form, together with the ring

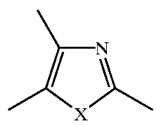

a condensed ring represented by formula

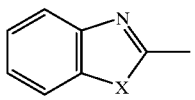

which may be substituted with an optionally substituted $C_{1-6}$ alkyl group, an amino group, a cyano group, a nitro group, a hydroxyl group, a halogen atom or a $C_{1-5}$ alkoxy group, X is an oxygen atom, a nitrogen atom, a sulfur atom or —CH=CH—, R3 is an optionally substituted phenylsulfonylamino group, an optionally substituted phenylsulfonyl group or an optionally substituted phenylsulfoxide group, n is an integer of from 2 to 6, A is —O—B—, —B—O—, —S—B—, —B—S— or —B—, and B is a $C_{1-6}$ alkylene group or a $C_{2-5}$ alkenylene group, provided that the cases wherein R1 is a $C_{1-6}$ alkyl group, a $C_{3-8}$ cycloalkyl group or a phenyl group, R2 is a hydrogen atom, A is a vinylene group, and X is a sulfur atom are excluded) or salts thereof, benzaldehyde derivatives represented by general formula (IIIa):

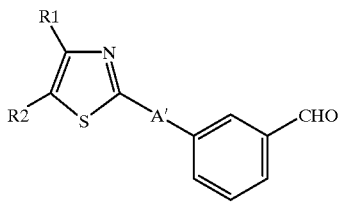

(wherein R1 and R2 which may be the same or different, are hydrogen atoms, $C_{3-8}$ cycloalkyl groups, optionally substituted $C_{1-6}$ alkyl groups, optionally substituted aryl groups or form, together with the ring

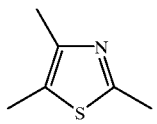

a condensed ring represented by formula

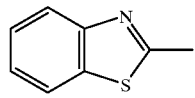

which may be substituted with an optionally substituted $C_{1-6}$ alkyl group, an amino group, a cyano group, a nitro group, a hydroxyl group, a halogen atom or a $C_{1-5}$ alkoxy group, A' is —B'—O— or —B'—, and B' is a $C_{1-6}$ alkylene group) or salts thereof, benzonitrile derivatives represented by general formula (IV):

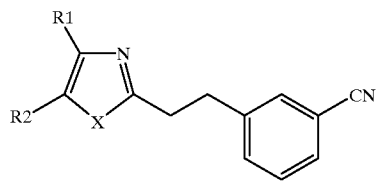

(wherein RI and R2 which may be the same or different, are hydrogen atoms, $C_{3-8}$ cycloalkyl groups, optionally substituted $C_{1-6}$ alkyl groups, optionally substituted aryl groups or form, together with the ring

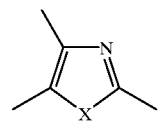

a condensed ring represented by formula

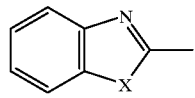

which may be substituted with an optionally substituted $C_{1-6}$ alkyl group, an amino group, a cyano group, a nitro group, a hydroxyl group, a halogen atom or a $C_{1-5}$ alkoxy group, and X is an oxygen atom, a nitrogen atom, a sulfur atom or —CH=CH—)or salts thereof and amine derivatives represented by general formula (V):

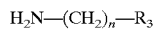

$H_2N—(CH_2)_n—R_3$ (wherein n is an integer of from 2 to 6, and R3 is an optionally substituted phenylsulfonylamino group, an optionally substituted phenylsulfonyl group or an optionally substituted phenylsulfoxide group) or salts thereof. The present invention further provides a pharmaceutical, anti-allergic agent and leukotriene and thromboxane $A_2$ antagonistic agent containing a 2-sulfamoylbenzoic acid derivative represented by general formula (I) or a salt, hydrate or solvate thereof as an active ingredient.

In general formulae (I), (II), (IIIa), (IV) and (V) mentioned above, a "$C_{3-8}$ cycloalkyl group" is a cyclopropyl group, a cyclobutyl group, a cyclopentyl group, a cyclohexyl group, a cycloheptyl group or a cyclooctyl group, preferably a cyclopropyl group or a cyclobutyl group.

A "$C_{1-6}$ alkyl group" is a linear or branched alkyl group such as a methyl group, an ethyl group, a propyl group, an isopropyl group, a n-butyl group, an isobutyl group, a tert-butyl group, a n-pentyl group or a n-hexyl group, preferably an isopropyl group or a tert-butyl group.

An "optionally substituted aryl group" is a carbocyclic aryl group such as a phenyl group or a naphthyl group, which may have, as a substituent, a halogen atom such as a fluorine atom, a chlorine atom, a bromine atom or an iodine atom, a $C_{1-6}$ alkyl group such as a methyl group or an ethyl group or a $C_{1-5}$ alkoxy group such as a methoxy group or an ethoxy group, preferably a fluorine atom, a chlorine atom, a bromine atom, a methyl group or a methoxy group.

A "halogen atom" is a fluorine atom, a chlorine atom, a bromine atom or an iodine atom.

A "$C_{1-5}$ alkoxy group" is a methoxy group, an ethoxy group, a n-propoxy group, a n-butoxy group, an isobutoxy group, a tert-butoxy group or a n-pentoxy group, preferably a methoxy group or an ethoxy group.

An "optionally substituted phenylsulfonylamino group", an "optionally substituted phenylsulfonyl group" and an "optionally substituted phenylsulfoxide group" may have, as a substituent, a halogen atom such as a fluorine atom, a chlorine atom, a bromine atom or an iodine atom, a $C_{1-6}$ alkyl group such as a methyl group or an ethyl group or a $C_{1-5}$ alkoxy group such as a methoxy group or an ethoxy group, preferably a fluorine atom, a chlorine atom, a bromine atom, a methyl group or a methoxy group, at the ortho-position, meta-position, or para-position, preferably at the para-position.

An "ester residue" is an ester residue such as a $C_{1-6}$ alkyl group, a benzyl group, a phenethyl group or a 1-naphthyl group or an ester group metabolically hydrolysable in vivo such as a lower alkanoyloxy lower alkyl group like an acetyloxymethyl group, a lower alkenoyl lower alkyl group like a vinylcarbonylmethyl group, a cycloalkylcabonyloxy lower alkyl group like a cyclopropylcarbonyloxymethyl group, a lower alkenoyloxy lower alkyl group like a vinyl-caronyloxymethyl group, a lower alkoxy lower alkyl group like a methoxymethyl group, a lower alkoxy lower alkoxy lower alkyl group like a methoxymethoxymethyl group, a lower alkoxycarbonyloxy lower alkyl group like a methoxycarbonyloxymethylmethyl group, a benzoyloxy lower alkyl group like a benzoyloxymethyl group, a 2-oxotetrahydrofuan-5-yl group or a 2-oxo-5-(lower alkyl)-1,3-dioxolen-4-ylmethyl group. Herein, "lower" means a linear or branched carbon chain having a carbon number of 1 to 6.

A "$C_{1-6}$ alkylene group" is a linear or branched alkylene group such as a methylene group, an ethylene group, a methylmethylene group, a trimethylene group, a propylene group, a dimethylmethylene group, a tetramethylene group, a 1-methyltrimethylene group, a 2-methyltrimethylene group, a 3-methyltrimethylene group, a 1-ethylethylene group, a 2-ethylethylene group, 2,2-dimethylethylene, 1,1-dimethylethylene, an ethylmethylmethylene group, a pentamethylene group, 1-methyltetramethylene, 2-methyltetramethylene, a 3-methyltetramethylene group, a 4-methyltetramethylene group, a 1,1-dimethyltrimethylene group, a 2,2-dimethyltrimethylene group, a 3,3-dimethyltrimethylene group, a 1,3-dimethyltrimethylene group, a 2,3-dimethyltrimethylene group, 1,2-dimethyltrimethylene, a 1,1,2-trimethylethylene group, a diethylmethylene group, a hexamethylene group, a 1-methylpentamethylene group, a 1,1-dimethyltetramethylene group or a 2,2-dimethyltetramethylene group, preferably a methylene group, an ethylene group, a propylene group, a methylmethylene group or a dimethylmethylene group.

A "$C_{2-5}$ alkenylene group" is a vinylene group, a propenylene group or a butenylene group, preferably a vinylene group.

The present invention covers the racemic bodies, diastereomers and any optical isomers of compounds of the present invention represented by general formulae (I), (II), (IIIa), (IV) and (V) which have one or more asymmetric carbon atom. Further, the present invention also covers any geometrical isomers of the compounds of the present invention inclusive of the (E)-forms, (Z)-forms and mixtures thereof.

The pharmaceutically acceptable salts useful in the formulae (I), (II), (IIIa), (IV) and (V) of the invention include inorganic salts such hydrohalides such as hydrofluorides, hydrochlorides, hydrobromides and hydroiodides, nitrates, perchlorates, sulfates, phosphates and carbonates, lower alkylsulfonates such as methanesulfonates, trifluoromethanesulfonates and ethanesulfonates, arylsulfonates such as benzenesulfonates and p-toluenesulfonates, carboxylates such as acetates, fumarates, succinate, citrates, tartrates, oxalates and maleates, amino acid salts such as glycine salts, alanine salts, glutamates and aspartates and alkali metal salts such as sodium salts and potassium salts. The pharmaceutically acceptable solutions which can form a solvate with the compound according to the present invention include solvates with acetone, 2-butanol, 2-propanol, ethanol, ethyl acetate, tetrahydrofuran and diethyl ether.

The compounds of the present invention represented by general formulae (I), (II), (IIIa), (IV) and (V) can be produced by the processes described below.

[Process A] Process for producing the compounds of the present invention represented by general formulae (I) and (II)

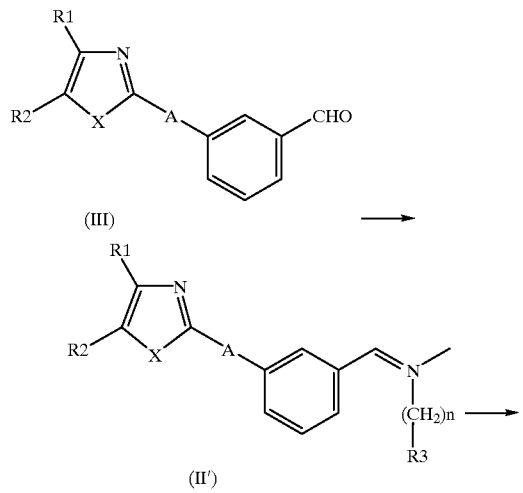

-continued

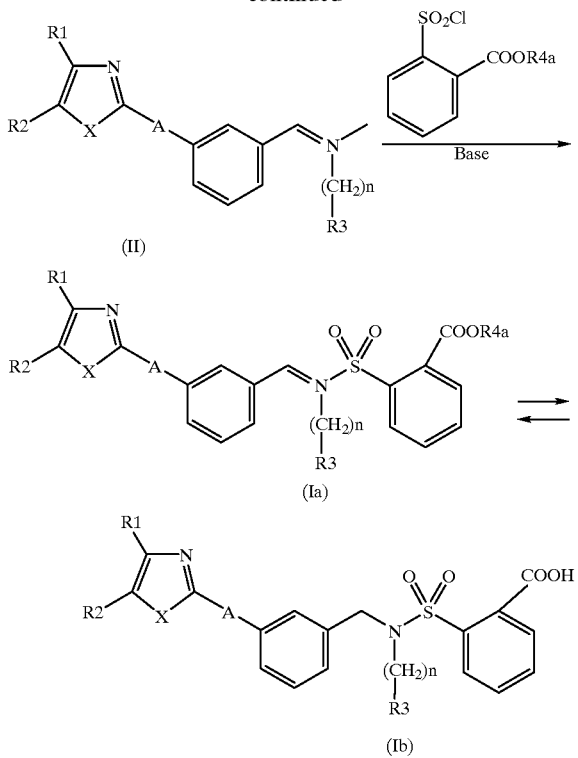

(II)

(Ia)

(Ib)

(wherein R1, R2, X, R3, n and A are the same as defined above, and R4a is an ester residue.)

The first step is conventional reductive amination of an aldehyde represented by general formula (III) with an amine represented by general formula (V) and yields a benzylamine derivative represented by general formula (II).

This step is usually accomplished by in situ formation of an intermediary imine represented by general formula (II') from the aldehyde represented by general formula (III) and the amine represented by general formula (V) followed by reduction with an appropriate reducing agent. For formation of the intermediary imine, as the reaction solvent, methanol, ethanol, isopropanol, benzene or toluene is preferable, though there is no particular restriction unless the reaction is considerably inhibited. The reaction temperature is preferably from 20° C. to 140° C., and the reaction time is preferably from 1 to 24 hours. For reduction of the intermediary imine, as the reducing agent, for example, isodium borohydride or lithium aluminum hydride is preferable, though any usual reducing agent that can reduce an imino group to an amino group can be used without any particular restriction. With respect to the amounts of the respective reactants, the compound of general formula (V) is used preferably in an amount of 1 to 5 equivalents based on the compound of general formula (III), and the reducing agent is used preferably in an amount of from 1 to 5 equivalents based on the compound of general formula (III). The reaction solvent is preferably methanol, ethanol or isopropanol though there is no particular restriction unless the reaction is considerably inhibited. The reaction temperature is preferably from 0° C. to 70° C., and the reaction time is preferably from 30 minutes to 12 hours.

The second step is conventional sulfonamidation of the benzylamine derivative (II) obtained in the first step with a 2-chlorosulfonylbenzoic acid ester in the presence of a base and yields a 2-sulfamoylbenzoic acid derivative (Ia) which has an ester residue as R4 in general formula (I). The base may be either an aliphatic amine or an aromatic amine, preferably triethylamine or pyridine. With respect to the amounts of the respective reactants, the 2-chlorosulfonylbenzoic acid ester is used preferably in an amount of 1 to 3 equivalents based on the benzylamine derivative (II), and the base is used preferably in an amount of from 1 to 5 equivalents based on the benzylamine derivative (II). The reaction solvent is preferably chloroform, dichloromethane, 1,2-dichloroethane or 1,1,2, 2-tetrachloroethane, though there is no particular restriction unless the reaction is considerably inhibited. The reaction temperature is preferably from 0° C. to 100° C., and the reaction time is preferably from 30 minutes to 12 hours.

The third step is conventional hydrolysis of the compound of general formula (Ia) obtained in the second step and yields a compound of the present invention, wherein R4 is a hydrogen atom, represented by general formula (Ib). For this reaction, conventional hydrolysis in the presence of a base may be employed. The base is preferably a metal hydroxide or metal carbonate such as sodium hydroxide, potassium hydroxide, sodium carbonate or potassium carbonate. With respect to the amounts of the respective reactants, the base is used preferably in an amount of 1 to 50 equivalents based on the ester compound (Ia). The reaction solvent is preferably water, methanol, ethanol, tetrahydrofuran or a mixture thereof though there is no particular restriction unless the reaction is considerably inhibited. The reaction temperature is preferably from 0° C. to 100° C., and the reaction time is preferably from 30 minutes to 24 hours.

A compound (Ia) of the present invention is also obtainable by esterification of a compound (Ib) of the present invention which comprises conversion of the compound (Ib) of the present invention into an acid halide with a halogenating agent such as thionyl chloride, oxalyl chloride or thionyl bromide followed by treatment with an alcohol in the presence or absence of a base. For formation of the acid halide, as the reaction solvent, dichloromethane, chloroform, 1,2-dichloroethane, 1,1,2,2-tetrachloroethane or toluene is preferable, though there is no particular restriction unless the reaction is considerably inhibited. The reaction temperature is preferably from 0° C. to 100° C., and the reaction time is preferably from 1 to 12 hours.

The base used for the esterification may be either an aliphatic amine or an aromatic amine, preferably triethylamine or pyridine. With respect to the amounts of the respective reactants, the alcohol is used preferably in an amount of from 1 to 10 equivalents based on the acid halide, and the base is used preferably in an amount of from 1 to 5 equivalents based on the acid halide. The reaction solvent may be dichloromethane, chloroform, 1,2-dichloroethane, 1,1,2,2-tetrachloroethane, toluene or the alcohol used for the esterification, though there is no particular restriction unless the reaction is considerably inhibited. The reaction temperature is preferably from 0° C. to 80° C., and the reaction time is preferably from 30 minutes to 12 hours.

A compound (Ia) of the present invention is also obtainable from a compound (Ib) of the present invention through reaction with an alcohol using a condensing agent such as dicyclohexylcarbodiimide, 1-ethyl-3-(3'-dimethylaminopropyl)carbodiimide or 1,1'-carbonyldiimidazol. The condensing agent is used preferably in an amount of from 1 to 2 equivalents based on the compound (Ib) of the present invention. The reaction solvent is preferably N,N-dimethylformamide, dimethyl sulfoxide, tetrahydrofuran, dioxane, dichloromethane, chloroform or 1,2-dichloroethane though there is no particular restriction unless the reaction is considerably inhibited. The reaction temperature is preferably from 0° C. to 70° C., and the reaction time is preferably from 1 to 48 hours. In the cases of some types of reaction solvents, more than one equivalent of N-hydroxysuccinimide or N-hydroxybenzotriazole may be added beforehand so that the reaction proceeds smoothly.
[Process B] Process for producing the compounds (IIIb) of general formula (III) wherein X is a sulfur atom, and A is —CH$_2$O—

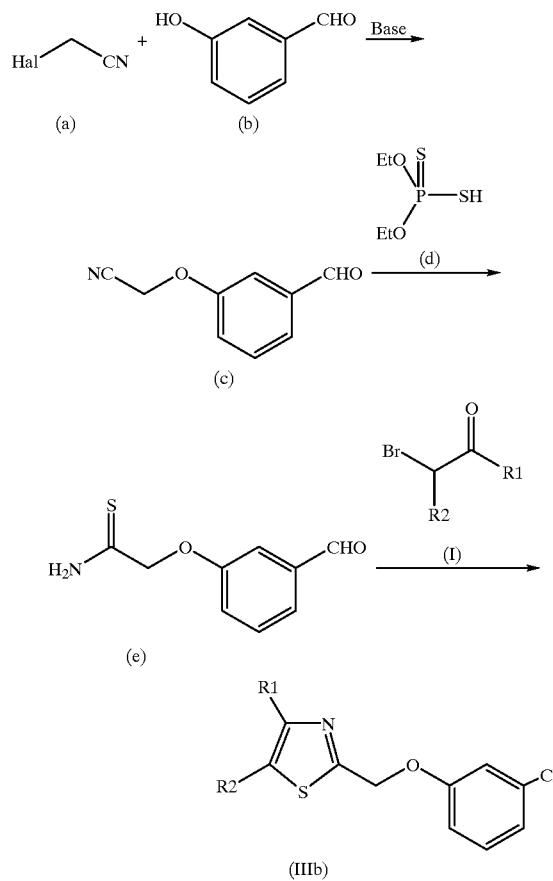

(wherein R1 and R2 are the same as defined above except that they do not form a condensed ring, and Hal is a bromine atom or a chlorine atom.)

Firstly, a compound represented by formula (a) reacts with a compound (b) in the presence of a base to give a compound (c). The base used for the reaction is preferably a metal carbonate such as potassium carbonate or sodium carbonate or a metal hydride such as sodium hydride or potassium hydride. As the reaction solvent, N,N-dimethylformamide, dimethyl sulfoxide or acetone may be mentioned, though there is no particular restriction unless the reaction is considerably inhibited. The reaction temperature is preferably from 0° C. to 100° C., and the reaction time is preferably from 30 minutes to 8 hours. Then, the resulting compound (c) reacts with O,O-diethyl dithiophosphate (d) to give a compound (e). For the reaction, O,O-diethyl dithiophosphate is used preferably in an amount of from 1 to 5 equivalents based on the compound (c). The reaction solvent is preferably water or a solvent mixture of an organic solvent/water, though there is no particular restriction unless the reaction is considerably inhibited, and as the organic solvent, dimethoxyethane, tetrahydrofuran or acetone is preferable. The reaction temperature is preferably from 25° C. to 100° C., and the reaction time is preferably from 30 minutes to 8 hours. The resulting compound (e) reacts with a bromoketone represented by formula (f) to give a compound represented by general formula (IIIb). With respect to the amounts of the respective reactants, the bromoketone represented by formula (f) is used preferably in an amount of from 1 to 2 equivalents based on the compound (e). The reaction solvent is preferably a lower alcohol such as methanol, ethanol or isopropanol though there is no particular restriction unless the reaction is considerably inhibited. The reaction temperature is preferably from 25° C. to 100° C., and the reaction time is preferably from 30 minutes to 24 hours.

[Process C] Process for producing the compounds (IIIc) of general formula (III) wherein A is —CH$_2$O—

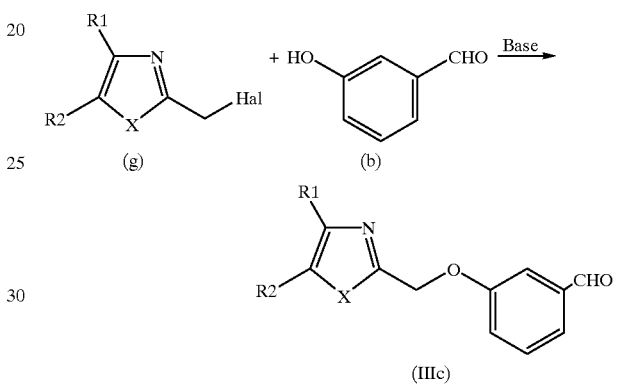

(wherein R1, R2, X and Hal are the same as defined above.)

A compound represented by formula (g) and a compound (b) undergo alkylation in the presence of a base to give a compound represented by general formula (IIIc). As the base used for the reaction, a metal carbonate such as potassium carbonate or sodium carbonate or a metal hydroxide such as sodium hydride or potassium hydride is ipreferable, and the base is used preferably in an amount of from 1 to 10 equivalents based on the compound (b). As the reaction solvent, N,N-dimethylformamide, dimethyl sulfoxide or acetone may be mentioned, though there is no particular restriction unless the reaction is considerably inhibited. The reaction temperature is preferably from 30° C. to 100° C., and the reaction time is preferably from 30 minutes to 8 hours.

[Process D] Process for producing the compounds (IIId) of general formula (III) wherein A is an ethylene group and the compounds of the present invention represented by general formula (IV)

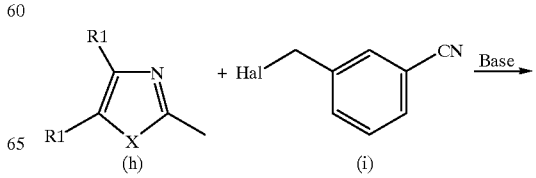

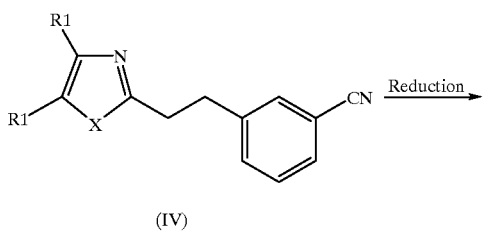

(IV)

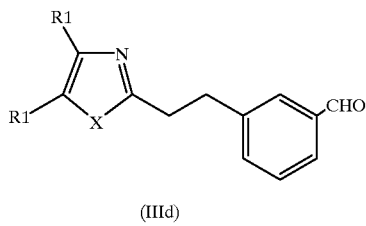

(IIId)

(wherein R1, R2, X and Hal are the same as defined above.)

A compound represented by formula (h) reacts with a compound (i) in the presence of a base to give a compound represented by formula (IV). As the base, an alkyl metal salt such as n-butyllithium, tert-butyllithium, lithium disiopropylamide or potassium tert-butoxide is preferably used. The base is used preferably in an amount of from 1 to 5 equivalents based on the compound of formula (h). As the reaction solvent, tetrahydrofuran, diethyl ether or toluene is preferable, though there is no particular restriction unless the reaction is considerably inhibited. The reaction temperature is preferably from −100° C. to 50° C., and the reaction time is preferably from 30 minutes to 12 hours. The subsequent reduction of the nitrile group in the resulting compound represented by general formula (IV) with a reducing agent affords a compound represented by general formula (IIId). The reducing agent is preferably a metal hydride, particularly diisopropylaluminum hydride, though any reducing agent that can reduce a nitrile group into an aldehyde group may be used without any no particular restriction, and used in an amount of from 1 to 2 equivalents based on the compound of general formula (IV). As the reaction solvent, tetrahydrofuran, diethyl ether or toluene may be mentioned, though there is no particular restriction unless the reaction is considerably inhibited. The reaction temperature is preferably from −100° C. to 50° C., and the reaction time is preferably from 30 minutes to 12 hours.

[Process E] Process for producing the compounds (IIId) of general formula (III) wherein A is an ethylene group

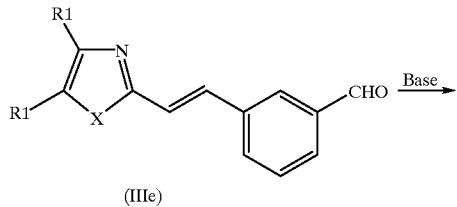

(IIIe)

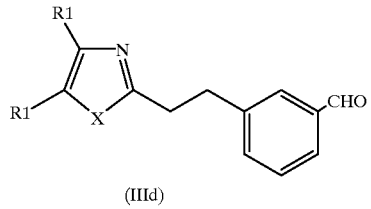

(IIId)

(wherein R1, R2 and X are the same as defined above.)

Catalytic hydrogenation of a compound represented by general formula (IIIe) in the presence of a catalyst affords a compound represented by general formula (IIId). As the hydrogenation catalyst, 5% palladium carbon, 10% palladium carbon, 30% palladium carbon, platinum oxide or Wilkinson's catalyst is preferable. The catalyst is used preferably in an amount of from 1/10 to 1 time the weight of the compound (IIIe), and the hydrogen pressure is preferably from 1 to 5 atm. As the reaction solvent, methanol, ethanol, ethyl acetate or tetrahydrofuran is preferable, though there is no particular restriction unless the reaction is considerably inhibited. The reaction temperature is preferably from 25° C. to 70° C., and the reaction time is preferably from 1 to 72 hours.

[Process F] Process for producing the compounds (Va) of general formula (V) wherein R3 is an optionally substituted phenylsulfonyl group

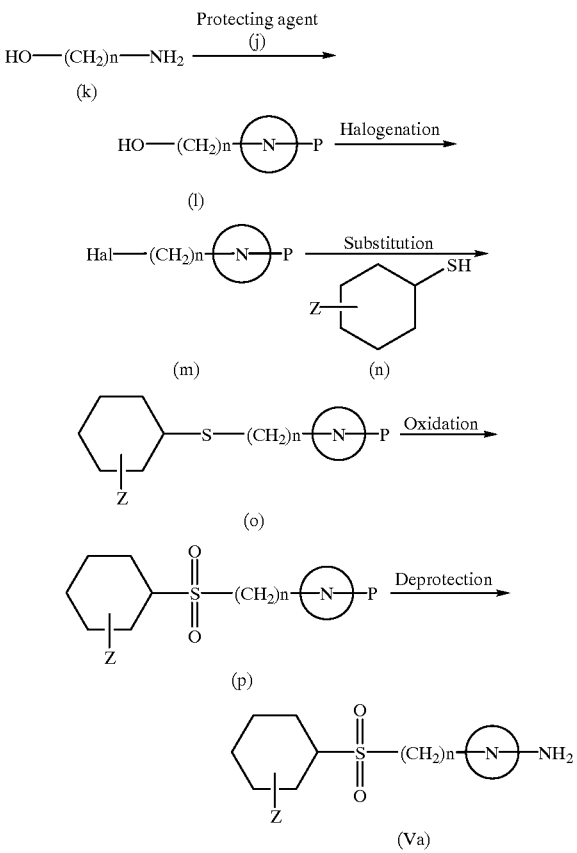

(wherein n and Hal are the same as defined above, P is a protecting group, and Z is a hydrogen atom, a halogen atom, a $C_{1-6}$ alkyl group or a $C_{1-5}$ alkoxy group.)

An amino alcohol compound represented by formula (k) is converted into a compound of general formula (l) for protection of the amino group. The protection of the amino group can be accomplished by a conventional method using a protecting group such as a phthalimido group, a tert-butoxycarbonyl group or a benzyloxycarbonyl group. The resulting compound of formula (l) is converted into a compound of formula (m) by replacement of the hydroxyl group with a halogen atom. The halogenation can be accomplished conventionally by bromination using phosphorus tribromide or carbon tetrabromide/triphenylphosphine or chlorination using thionyl chloride or phosphorus pentachloride. The resulting compound of formula (m) reacts with a thiophenol of formula (n) to give a compound of formula (o). The substitution can be accomplished by using a base such as potassium carbonate or sodium hydride. The resulting compound of formula (o) is oxidized to a compound represented by formula (p) and then finally converted into a compound of general formula (Va) through deprotection. For the oxidation, an oxidizing agent such as metachloroperbenzoic acid may be used. For the deprotection, conventional methods may be used according to the protecting group.

[Process G] Process for producing the compounds (Vb) of general formula (V) wherein R3 is an optionally substituted phenylsulfonylamino group

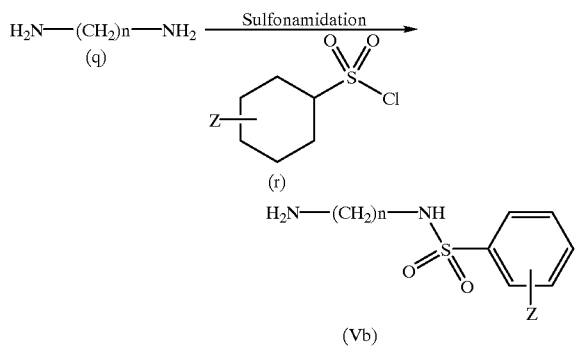

(wherein n and Z are the same as defined above.)

A diamine compound represented by formula (q) reacts with a phenylsulfonyl chloride represented by formula (r) to give a compound of general formula (Vb). With respect to the amounts of the respective reactants, the diamine compound (q) is used preferably in an amount of from 1 to 20 equivalents based on the compound of formula (r). As the reaction solvent, chloroform, 1,2-dichloroethane, dichloromethane or 1,1,2,2-tetrachloroethane may be mentioned, though there is no particular restriction. The reaction temperature is preferably from 0° C. to 50° C., and the reaction time is preferably from 1 to 8 hours.

The compounds of the present invention and intermediates produced in the above-mentioned processes can be isolated in the forms of free compounds, salts, hydrates, solvates with various solvents such as ethanol or polymorphic crystals. Pharmaceutically acceptable salts of the compounds of the present invention are obtainable by conventional salt-forming reactions. Isolation can be accomplished through chemical techniques such as fractional extraction, crystallization and various types of fractional chromatography. Their optical isomers can be obtained as stereochemically pure isomers from appropriately selected starting materials or by racemic resolution of racemic compounds.

The 2-sulfamoylbenzoic acid derivatives of general formula (I) thus obtainable have an excellent anti-allergic effect by virtue of their antagonistic effects on both the $LTD_4$ receptor and the $TXA_2$ receptor and show excellent effects as preventive and therapeutic agents on allergic bronchial asthma, rhinitis and conjunctivitis, atopic dermatitis, gastroenteritis, colitis, vernal catarrh, nephritis and other allergic diseases. They are also useful as preventive and therapeutic agents for diseases associated with leukotrienes and $TXA_2$ and widely applicable for prevention and treatment of ischemic heart and brain diseases, angina pectoris, inflammatory peptic ulcer and hepatopathy.

The 2-sulfamoylbenzoic acid derivatives of the present invention can be used by themselves or by using known drug formulations in various dosage forms, for example, for oral pharmaceuticals such as tablets, capsules, granules, fine granules, powders, liquids and syrups and for parenteral pharmaceuticals such as injections, nasal drops, eye drops, infusions, ointments, suppositories, inhalants, percutaneous pharmaceuticals and patches.

The dosages of the medicines of the present invention depend on the condition, age and body weight of the patient, the therapeutic effect and the mode and term of administration, but in the case of oral administration to an adult, they are usually administered in an amount of from 0.1 mg to 10 g per day.

BEST MODE FOR CARRYING OUT THE INVENTION

EXAMPLES

Now, the compounds of the present invention and their preparations will be described in further detail with reference to Examples. However, the present invention should not be restricted to these specific Examples. The $H^1$-NMR spectra were obtained by means of a spectrometer, model JNM-EX270 (270 MHz, JEOL Ltd.) by using tetramethylsilane (TMS) as an internal standard, and the δ values were given in ppm. The DI-EI mass spectra were obtained by means of a spectrometer, model QP1000EX (Shimadzu Corporation). The FAB mass spectra were obtained by means of a high resolution mass spectrometer, model JMN-HX110A (JEOL Ltd.).

Example 1

Preparation of 3-[(4-isopropyl-2-thiazolyl)methoxy] benzaldehyde 50 g (0.41 mol) of m-hydroxybenzaldehyde and 49 g (0.41 mol) of bromoacetonitrile were dissolved in 300 ml of N,N-dimethylformamide and stirred together with 85g (0.62 mol) of potassium carbonate and 6.0 g (0.04 mol) of sodium iodide at room temperature for 1.5 hours. The solvent was distilled off in vacuo, and then water and ethyl acetate were added for extraction. The ethyl acetate layer was washed with saturated aqueous sodium chloride and dried over magnesium sulfate and evaporated in vacuo for removal of the solvent. The residue was purified by silica gel column chromatography (eluent; chloroform) to give 58 g of 3-cyanomethoxybenzaldehyde in a yield of 88%.

$^1$H-NMR(CDCl$_3$):4.86(2H,s) 7.25–7.30(1H,m) 7.44–7.64 (3H,m) 10.01(1H,s).

Then, 50 g (0.31 mol) of 3-cyanomethoxybenznaldehyde was dissolved in 500 ml of 1,2-dimethoxyethane and stirred together with 5.6 ml (0.31 mol) of water and 52 ml (0.31 mol) of O,O-diethyl dithiophosphate at 70° C. for 3 hours. The solvent was distilled off in vacuo, and the residue was washed with ether and filtered off to give 31 g of 3-(thiocarbamoylmethoxy)benzaldehyde in a yield of 51%.

Mass(m/z):195(M+) 160 121; $^1$H-NMR(CDCl$_3$):4.94(2H, s) 7.20–7.29(1H,m) 7.44–7.58(3H,m) 7.97(2H,br) 9.99(1H, s).

Then, 32.9 g (0.38 mol) of methyl isopropyl ketone was dissolved in 291 ml of methanol and mixed with 2.9 ml of 25% HBr-AcOH under cooling with ice. 18.7 ml (0.36 mol) of bromine was added dropwise under cooling with ice, and the reaction solution was stirred for 2 hours. The reaction solution was stirred together with water at room temperature for 30 minutes and then together with 3-(thiocarbamoylmethoxy)benzaldehyde at room temperature for 5.5 hours. Water and saturated sodium hydrogen carbonate were added to adjust the pH to 8.0, and the reaction solution was extracted with ethyl acetate. The ethyl acetate layer was washed with saturated aqueous sodium chloride, dried over anhydrous magnesium sulfate and evaporated in vacuo for removal of the solvent, and the residue was purified by silica gel column chromatography (eluent; n-hexane:ethyl acetate=20:1) to give 64.3 g of the title compound in a yield of 68%.

$^1$H-NMR(CDCl$_3$): 1.33(6H,d,J=6.9 Hz) 3.12(1H,) 5.40 (2H,s) 6.92(1H,d,J=0.99 Hz) 7.26–7.31(1H,m) 7.47–7.54 (3H,m) 9.98(1H,s).

Similarly, the compounds of Example 2 and 3 were prepared.

Example 2

3-[(4-Cyclobutyl-2-thiazolyl)methoxy]benzaldehyde

Mass(m/z):273(M+) 254 152; $^1$H-NMR(CDCl$_3$): 1.90–2.10(2H,m) 2.20–2.43(4H,m) 3.68(1H,quint) 5.40(2H, s) 6.94(1H,s) 7.26–7.30(1H,m) 7.47–7.54(3H,m) 9.98(1H, s).

Example 3

3-[(4-Cyclopropyl-2-thiazolyl)methoxy] benzaldehyde $^1$H-NMR(CDCl$_3$): 0.86–1.00(4H,m) 2.06(1H,m) 5.35 (2H,s) 6.87(1H,s) 7.24–7.31(1Hm) 7.44–7.53(3H,m)9.98 (1H,s).

Example 4

Preparation of 3-[2-(4-cyclobutyl-2-thiazolyl)ethyl] benzonitrile 766 mg (5 mmol) of 4-cyclobutyl-2-methylthiazole was dissolved in 15 ml of anhydrous tetrahydrofuran and mixed with 561 mg (5 mmol) of potassium tert-butoxide, and 3 ml (5 mmol) of n-butyllithium (1.68M hexane solution) was added dropwise at –78° C. After 3 hours of stirring at the same temperature, 1270 mg (6 mmol) of 3-bromomethylbenzonitrile in 3 ml anhydrous tetrahydrofuran was added dropwise, and the reaction solution was stirred for one hour and 40 minutes. After addition of saturated aqueous ammonium chloride, the reaction solution was extracted with diethyl ether twice, and the organic layer was washed with saturated aqueous sodium chloride, dried over anhydrous magnesium sulfate and evaporated in vacuo for removal of the solvent. The residue was purified by silica gel column chromatography (eluent; n-hexane:ethyl acetate=4:1) to give 876 mg of the title compound as a yellow oily substance in a yield of 64%.

Mass(m/z): 268(M+); $^1$H-NMR(CDCl$_3$): 1.84–2.11(2H, m) 2.15–2.42(4H,m) 3.11–3.19(2H,m) 3.25–3.52(2H,m) 3.57–3.70(1H,m) 6.75(1H,s) 7.35–7.52 (4H,m).

Example 5

Preparation of 3-[2-(4-cyclobutyl-2-thiazolyl)ethyl] benzaldehyde 875 mg (3.3 mmol) of 3-[2-(4-cyclobutyl-2-thiazolyl) ethyl]benzonitrile was dissolved in 20 ml of toluene, and 3.6 ml (3.60 mmol) of 1.01M diisobutylaluminum hydride (toluene solution) was added at –78° C. The reaction solution was brought back to room temperature and stirred for 2 hours. The reaction solution was mixed with saturated aqueous ammonium chloride and 2N hydrochloric acid successively and stirred for 1 hour, and the organic layer was washed with saturated aqueous sodium hydrogen carbonate and saturated aqueous sodium chloride, dried over anhydrous magnesium sulfate and evaporated in vacuo for removal of the solvent. The residue was purified by silica gel column chromatography (eluent; n-hexane:ethyl acetate= 4:1) to give 792 mg of the title compound as a colorless oily substance in a yield of 89%.

Mass(m/z): 271(M+) 242; $^1$H-NMR(CDCl$_3$): 1.84–2.42 (6H,m) 3.20(2H,m) 3.32(2H,m) 3.64(1H,quint) 6.74(1H,d) J=0.66 Hz) 7.47(2H,m) 7.73(2H,m) 9.99(1H,s).

Example 6

Preparation of 3-[2-(2-quinolyl)ethyl]benzaldehyde 5.5 g (21.2 mmol) of 3-[2-(2-quinolyl)ethenyl] benzaldehyde was dissolved in 500 ml and hydrogenated in the presence of 1.1 g of 10% palladium carbon at atmospheric pressure at room temperature for 10 hours under stirring. The 10% palladium carbon was filtered out through celite, and the filtrate was evaporated in vacuo. The residue was purified by silica gel column chromatography (eluent; n-hexane:ethyl acetate=9:1) to give 2.8 g (10.7 mmol) of the title compound in a yield of 51%.

Mass(m/z): 261(M+) 156; $^1$H-NMR(CDCl$_3$): 7.46–7.60 (3H,m) 7.65–7.91(6H,m) 8.05–8.17(3H,m) 10.07(1H,s)

Example 7

Preparation of 5-(4-chlorophenylsulfonyl) pentanamine 10 g (96.9 mmo)of 5-amino-1-pentanol was dissolved in 300 ml of toluene and refluxed together with 17.2 g (116 mmol) of phthalic anhydride at 120° C. for 24 hours. The solvent was distilled off in vacuo, and the residue was purified by silica gel column chromatography (eluent; chloroform) to give 16.6 g of 5-phthalimido-1-pentanol in a yield of 74%.

Mass(m/z): 233(M+) 203 160; $^1$H-NMR(CDCl$_3$): 1.37–1.48(2H,m) 1.58–1.78(4H,m) 3.62–3.73(4H,m) 7.68–7.74(2H,m) 7.81–7.87(2H,m).

Then, 16.2 g of 5-phthalimido-1-pentanol was dissolved in 350 ml of diethyl ether, and 4.3 ml of phosphorus tribromide was added dropwise at 0° C. The reaction solution was stirred at room temperature for 9 hours and neutralized with saturated aqueous sodium hydrogen carbonate, and the organic layer was washed with saturated aqueous sodium chloride, dried over anhydrous magnesium sulfate and evaporated in vacuo for removal of the solvent. The residue was purified by silica gel column chromatography (eluent; n-hexane:ethyl acetate=9:1) to give 9.2 g of 1-bromo-5-phthalimidopentane in a yield of 45%.

Mass(m/z): 296(M+) 216 160; $^1$H-NMR(CDCl$_3$): 1.44–1.55(2H,m) 1.63–1.77(2H,m) 1.86–2.00(2H,m) 3.37–3.42(2H,m) 3.67–3.73(2H,m) 7.68–7.75(2H,m) 7.81–7.88(2H,m).

Then, 9.2 g (31 mmol) of 1-bromo-5-phthalimidopentane was dissolved in 100 ml of N,N-dimethylformamide and stirred together with 8.6 g (62 mmol) of potassium carbonate, 465 mg (3.1 mmol) of sodium iodide and 4.5 g (31 mmol) of 4-chlorothiophenol at room temperature for 15 hours. The solvent was distilled off in vacuo, and water and ethyl acetate were added for extraction. The ethyl acetate layer was washed with saturated aqueous sodium chloride, dried over anhydrous magnesium sulfate and evaporated in vacuo for removal of the solvent. The residue was washed with hexane to give 9.6 g of 1-(4-chlorophenylthio)-5-phthalimidepentane in a yield of 86%.

Mass(m/z): 359(M+) 216 160; $^1$H-NMR(CDCl$_3$): 1.47–1.51(2H,m) 1.64–1.72(4H,m) 2.88(2H,t J=7.26 Hz) 3.68(2H,t J=7.26 Hz) 7.23(4H,s) 7.71–7.23(2H,m) 7.82–7.86(2H,m).

Then, 9.4 g (26.1 mmol) of 1-(4-chlorophenylthio)-5-phthalimidopentane was dissolved in 350 ml of 1,2-dichloroethane and stirred together with 9.9 g (57.4 mmol) of metachloroperbenzoic acid at room temperature for 18 hours. The reaction solution was washed with 5% sodium thiosulfate, 3% sodium hydrogen carbonate and saturated aqueous sodium chloride, dried over anhydrous magnesium sulfate and evaporated in vasuo for removal of the solvent to give 9.7 g of 1-(4-chlorophenylsulfonyl)-5-phthalimidopentane in a yield of 95%.

Mass(m/z): 391(M+) 216 160; $^1$H-NMR(CDCl$_3$): 1.37–1.48(2H,m) 1.61–1.81(4H,m) 3.05–3.11 (2H,m) 3.62–3.93(3H,m) 7.52–7.57(2H,m) 7.69–7.75(2H,m) 7.80–7.86(2H,m).

Then, 4.0 g (10.2 mmol) of 1-(4-chlorophenylsulfonyl)-5-phthalimidopentane was dissolved in 120 ml of dichloromethane and 20 ml of ethanol and stirred together with 6 ml of 80% hydrazine hydrate at room temperature for 36 hours. The impurities were filtered out, and the filtrate was evaporated in vacuo to give 3.2 g of the title compound.

Example 8

Preparation of 4-(4-chlorophenylsulfonylamino)butanamine 26.4 g (0.3 mol) of 1,4-diaminobutane was dissolved in 100 ml of 1,2-dichloroethene and stirred together with 6.3 g (0.03 mmol) of 4-chlorophenylsulfonyl chloride at room temperature for 4 hours. After addition of chloroform, the reaction solution was filtered through celite, and the filtrate was washed with water three times and with saturated aqueous sodium chloride successively, dried over anhydrous magnesium sulfate and evaporated in vacuo for removal of the solvent to give 5.1 g of the title compound in a yield of 65%.

Example 9

Preparation of N-[4-(4-chlorobenzenesulfonylamino)butyl]-3-[(4-isopropyl-2-thiazolyl)methoxy]benzylamine (Compound No.1a)

2.27 g (8.69 mmol) of 3-[(4-isopropyl-2-thiazolyl)methoxy]benzaldehyde and 2.27 g (8.69 mmol) of 4-(4-chlorophenylsulfonylamino)butanamine were dissolved in 150 ml of ethanol and refluxed together with 4.0 g of molecular sieves 3A for 16 hours. The molecular sieves 3A was filtered out, and the filtrate was stirred together with 873 mg of sodium borohydride at room temperature for 3 hours. The reaction solution was evaporated in vacuo for removal of ethanol as the solvent and mixed with water and ethyl acetate for ethyl acetate extraction. The ethyl acetate layer was washed with saturated aqueous sodium chloride, dried over anhydrous magnesium sulfate and evaporated in vacuo for removal of the solvent. The residue was purified by silica gel column chromatography (eluent; chloroform to chloroform:methanol=98:2) to give N-[4-(4-chlorobenzenesulfonylamino)butyl]-3-[(4-isopropyl-2-thiazolyl)methoxy]benzylamine (Compound No.1a).

Compouns Nos.2a to 90a were prepared similarly. The mass spectrum data are shown in Table 1.

TABLE 1

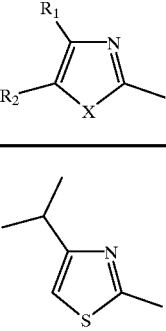

| Compound No. | 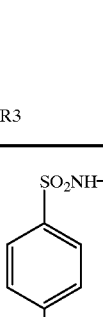 | A | R3 | n | FAB-MS (m/z) |
|---|---|---|---|---|---|
| 1a | (4-isopropyl-thiazolyl) | —CH$_2$O— | SO$_2$NH—(4-Cl-phenyl) | 4 | 508 (M$^+$) 315 246 |

TABLE 1-continued

[Structure: thiazole with R1, R2, X substituents connected via A to phenyl ring with CH2-NH-(CH2)n-R3]

| Compound No. | [thiazole with R1, R2, X, 2-methyl] | A | R3 | n | FAB-MS (m/z) |
|---|---|---|---|---|---|
| 2a | 4-cyclobutyl-2-methyl-thiazole | —CH$_2$O— | 4-F-C$_6$H$_4$-SO$_2$NH— | 4 | 504 (M$^+$), 330, 258 |
| 3a | 4-cyclobutyl-2-methyl-thiazole | —CH$_2$O— | 4-Br-C$_6$H$_4$-SO$_2$NH— | 4 | 566 (M$^+$), 331, 258 |
| 4a | 4-cyclobutyl-2-methyl-thiazole | —CH$_2$O— | 4-OCH$_3$-C$_6$H$_4$-SO$_2$NH— | 4 | 516 (M$^+$), 330, 258 |
| 5a | 4-cyclobutyl-2-methyl-thiazole | —CH$_2$O— | 4-CH$_3$-C$_6$H$_4$-SO$_2$NH— | 4 | 500 (M$^+$), 330, 258 |
| 6a | 4-cyclobutyl-2-methyl-thiazole | —CH$_2$O— | C$_6$H$_5$-SO$_2$NH— | 4 | 486 (M$^+$), 330, 258 |

TABLE 1-continued

| Compound No. | (R1/R2/X thiazole with cyclobutyl) | A | R3 | n | FAB-MS (m/z) |
| --- | --- | --- | --- | --- | --- |
| 7a | 4-cyclobutyl-2-methylthiazole | —CH₂O— | 4-Cl-C₆H₄-SO₂NH— | 3 | 506 (M⁺)<br>316<br>258 |
| 8a | 4-cyclobutyl-2-methylthiazole | —CH₂O— | 4-Cl-C₆H₄-SO₂NH— | 2 | 492 (M⁺)<br>302<br>258 |
| 9a | 4-cyclobutyl-2-methylthiazole | —CH₂O— | 4-Br-C₆H₄-SO₂NH— | 2 | 536 (M⁺)<br>301<br>258 |
| 10a | 4-cyclobutyl-2-methylthiazole | —CH₂O— | 4-F-C₆H₄-SO₂NH— | 2 | 476 (M⁺)<br>302<br>258 |
| 11a | 4-cyclobutyl-2-methylthiazole | —CH₂O— | C₆H₅-SO₂NH— | 2 | 458 (M⁺)<br>302<br>258 |

TABLE 1-continued

| Compound No. | $\begin{matrix} R_2 \\ X \end{matrix}\!\!\!\begin{matrix} R_1 \\ N \end{matrix}$ | A | R3 | n | FAB-MS (m/z) |
|---|---|---|---|---|---|
| 12a | 4-cyclobutyl-2-methylthiazole | —CH₂O— | 4-Cl-C₆H₄-SO₂NH— | 5 | 534 (M⁺) 344 258 |
| 13a | 4-cyclobutyl-2-methylthiazole | —CH₂O— | 4-Cl-C₆H₄-SO₂NH— | 4 | 520 (M⁺) 329 258 |
| 14a | 4-isopropyl-2-methylthiazole | —CH₂O— | 4-F-C₆H₄-SO₂NH— | 4 | 492 (M⁺) 318 246 |
| 15a | 4-isopropyl-2-methylthiazole | —CH₂O— | 4-Br-C₆H₄-SO₂NH— | 4 | 552 (M⁺) 317 246 |
| 16a | 4-isopropyl-2-methylthiazole | —CH₂O— | 4-OCH₃-C₆H₄-SO₂NH— | 4 | 504 (M⁺) 319 246 |

TABLE 1-continued

| Compound No. | R1 R2 X | A | R3 | n | FAB-MS (m/z) |
|---|---|---|---|---|---|
| 17a | 4-isopropyl, 2-methyl thiazole | —CH₂O— | SO₂NH—C₆H₄—CH₃ (4-methyl) | 4 | 488 (M⁺) 318 246 |
| 18a | 4-isopropyl, 2-methyl thiazole | —CH₂O— | SO₂NH—C₆H₅ | 4 | 474 (M⁺) 318 246 |
| 19a | 4-phenyl, 2-methyl thiazole | —CH₂O— | SO₂NH—C₆H₄—Cl (4-Cl) | 4 | 542 (M⁺) 352 280 |
| 20a | 4-cyclopropyl, 2-methyl thiazole | —CH₂O— | SO₂NH—C₆H₄—Cl (4-Cl) | 4 | 506 (M⁺) 316 244 |
| 21a | 4-cyclopropyl, 2-methyl thiazole | —CH₂O— | SO₂NH—C₆H₄—F (4-F) | 4 | 490 (M⁺) 316 244 |

TABLE 1-continued

Structure: R1, R2 on thiazole (X) ring connected via A to phenyl with CH2NH(CH2)nR3

| Compound No. | [thiazole with R1,R2,X] | A | R3 | n | FAB-MS (m/z) |
|---|---|---|---|---|---|
| 22a | 4-cyclopropyl-2-methyl thiazole | —CH$_2$O— | 4-Br-C$_6$H$_4$-SO$_2$NH— | 4 | 552 (M$^+$) 317 244 |
| 23a | 4-cyclopropyl-2-methyl thiazole | —CH$_2$O— | C$_6$H$_5$-SO$_2$NH— | 4 | 472 (M$^+$) 316 244 |
| 24a | 4-cyclopropyl-2-methyl thiazole | —CH$_2$O— | 4-CH$_3$-C$_6$H$_4$-SO$_2$NH— | 4 | 486 (M$^+$) 316 244 |
| 25a | 4-cyclopropyl-2-methyl thiazole | —CH$_2$O— | 4-OCH$_3$-C$_6$H$_4$-SO$_2$NH— | 4 | 502 (M$^+$) 316 244 |
| 26a | 4-cyclopropyl-2-methyl thiazole | —CH$_2$O— | 4-Cl-C$_6$H$_4$-SO$_2$NH— | 3 | 492 (M$^+$) 302 244 |

TABLE 1-continued

| Compound No. | X (thiazole with R1, R2) | A | R3 | n | FAB-MS (m/z) |
|---|---|---|---|---|---|
| 27a | 4-cyclopropyl, 2-methyl thiazole | —CH$_2$O— | 4-Cl-C$_6$H$_4$-SO$_2$NH— | 2 | 478 (M$^+$), 288, 244 |
| 28a | 4-cyclopropyl, 2-methyl thiazole | —CH$_2$O— | 4-F-C$_6$H$_4$-SO$_2$NH— | 2 | 462 (M$^+$), 288, 244 |
| 29a | 4-cyclobutyl, 2-methyl thiazole | —CH$_2$CH$_2$— | 4-Cl-C$_6$H$_4$-SO$_2$NH— | 4 | 518 (M$^+$), 328, 256 |
| 30a | 4-cyclobutyl, 2-methyl thiazole | —CH$_2$CH$_2$— | 4-Br-C$_6$H$_4$-SO$_2$NH— | 4 | 562 (M$^+$), 327, 256 |
| 31a | 4-cyclobutyl, 2-methyl thiazole | —CH$_2$CH$_2$— | C$_6$H$_5$-SO$_2$NH— | 4 | 485 (M$^+$), 329, 256 |

TABLE 1-continued
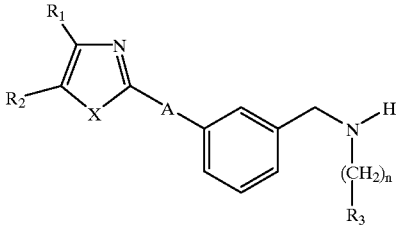
| Compound No. | 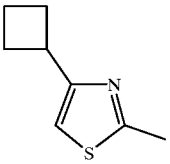 | A | R3 | n | FAB-MS (m/z) |
|---|---|---|---|---|---|
| 32a | 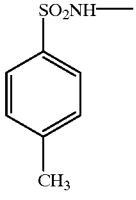 | —CH₂CH₂— | 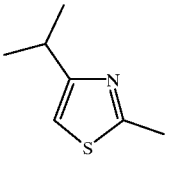 | 4 | 499 (M⁺) 329 256 |
| 33a | 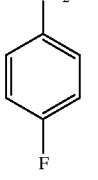 | —CH₂CH₂— | 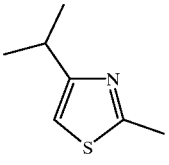 | 4 | 490 (M⁺) 316 244 |
| 34a | 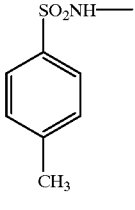 | —CH₂CH₂— | 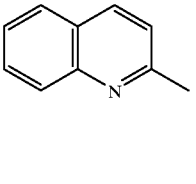 | 4 | 487 (M⁺) 317 244 |
| 35a | 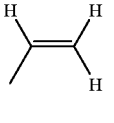 | 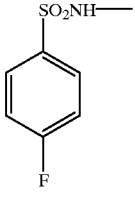 | 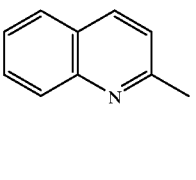 | 4 | 490 (M⁺) 316 244 |
| 36a | 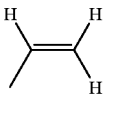 | 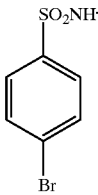 | | 4 | 550 (M⁺) 315 244 |

TABLE 1-continued
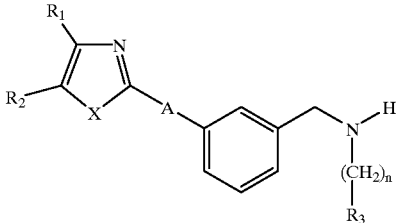
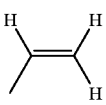
| Compound No. | | A | R3 | n | FAB-MS (m/z) |
|---|---|---|---|---|---|
| 37a | 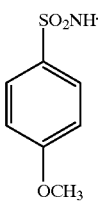 | H₂C=CH- (propenyl) | 4-OCH₃-C₆H₄-SO₂NH— | 4 | 502 (M⁺) 316 244 |
| 38a | 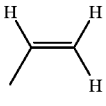 | propenyl | 4-CH₃-C₆H₄-SO₂NH— | 4 | 486 (M⁺) 316 244 |
| 39a | 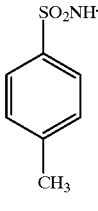 | propenyl | C₆H₅-SO₂NH— | 4 | 472 (M⁺) 316 244 |
| 40a | 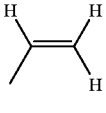 | propenyl | 4-Cl-C₆H₄-SO₂NH— | 3 | 492 (M⁺) 302 244 |
| 41a | 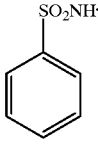 | propenyl | 4-Cl-C₆H₄-SO₂NH— | 2 | 479 (M⁺) 289 244 |
| 42a | 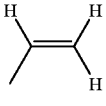 | propenyl | 4-Br-C₆H₄-SO₂NH— | 2 | 524 (M⁺) 289 278 |

TABLE 1-continued
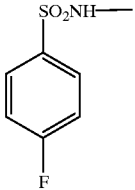
| Compound No. | | A | R3 | n | FAB-MS (m/z) |
|---|---|---|---|---|---|
| 43a | |  | | 2 | 462 (M+) 288 244 |
| 44a | | 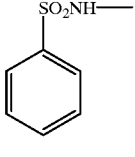 | | 2 | 444 (M+) 288 244 |
| 45a | |  | | 4 | 540 (M+) 350 278 |
| 46a | | 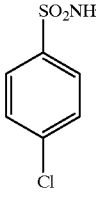 | | 4 | 519 (M+) 345 278 |
| 47a | |  | | 4 | 586 (M+) 351 278 |

TABLE 1-continued

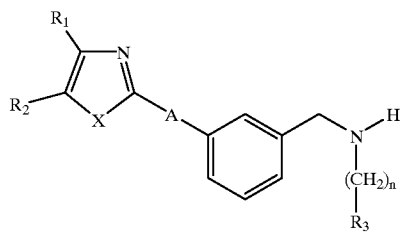

| Compound No. | (thiazole with R1, R2, X, 2-methyl) | A | R3 | n | FAB-MS (m/z) |
|---|---|---|---|---|---|
| 48a | 7-chloro-2-methylquinolin-yl | CH=CH(CH3) (trans) | 4-methoxyphenyl-SO2NH— | 4 | 536 (M+) 350 278 |
| 49a | 7-chloro-2-methylquinolin-yl | CH=CH(CH3) (trans) | 4-methylphenyl-SO2NH— | 4 | 520 (M+) 350 278 |
| 50a | 7-chloro-2-methylquinolin-yl | CH=CH(CH3) (trans) | phenyl-SO2NH— | 4 | 506 (M+) 350 278 |
| 51a | 7-chloro-2-methylquinolin-yl | CH=CH(CH3) (trans) | 4-chlorophenyl-SO2NH— | 3 | 526 (M+) 336 278 |
| 52a | 7-chloro-2-methylquinolin-yl | CH=CH(CH3) (trans) | 4-chlorophenyl-SO2NH— | 2 | 512 (M+) 322 278 |
| 53a | 2-methylquinolin-yl | —CH2O— | 4-fluorophenyl-SO2NH— | 4 | 494 (M+) 320 248 |

TABLE 1-continued
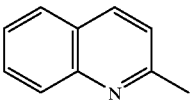
| Compound No. | 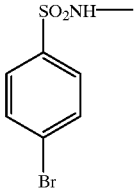 | A | R3 | n | FAB-MS (m/z) |
|---|---|---|---|---|---|
| 54a | 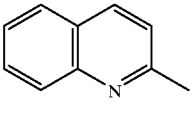 | —CH$_2$O— | 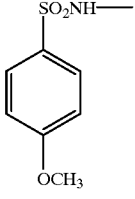 | 4 | 555 (M$^+$) 322 248 |
| 55a | 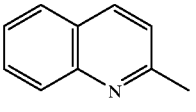 | —CH$_2$O— | 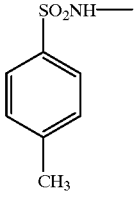 | 4 | 506 (M$^+$) 320 248 |
| 56a | 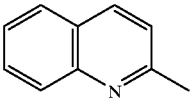 | —CH$_2$O— | 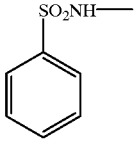 | 4 | 490 (M$^+$) 320 248 |
| 57a | 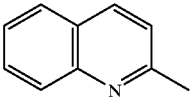 | —CH$_2$O— | 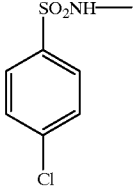 | 4 | 476 (M$^+$) 320 248 |
| 58a | | —CH$_2$O— | | 3 | 490 (M$^+$) 300 248 |

TABLE 1-continued

| Compound No. | R1/R2/X (ring) | A | R3 | n | FAB-MS (m/z) |
|---|---|---|---|---|---|
| 59a | 2-methylquinolin-yl | —CH₂O— | 4-Cl-C₆H₄-SO₂NH— | 2 | 482 (M⁺) 292 248 |
| 60a | 2-methylquinolin-yl | —CH₂O— | 4-F-C₆H₄-SO₂NH— | 2 | 466 (M⁺) 292 248 |
| 61a | 2-methylquinolin-yl | —CH₂O— | 4-Br-C₆H₄-SO₂NH— | 2 | 526 (M⁺) 291 248 |
| 62a | 2-methylquinolin-yl | —CH₂O— | C₆H₅-SO₂NH— | 2 | 449 (M⁺) 293 248 |
| 63a | 2-methylquinolin-yl | —CH₂O— | 4-Cl-C₆H₄-SO₂NH— | 5 | 537 (M⁺) 347 248 |
| 64a | 7-chloro-2-methylquinolin-yl | —CH₂O— | 4-Cl-C₆H₄-SO₂NH— | 2 | 516 (M⁺) 326 282 |

TABLE 1-continued
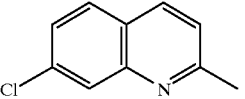
| Compound No. | 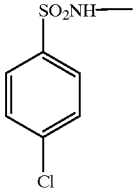 | A | R3 | n | FAB-MS (m/z) |
|---|---|---|---|---|---|
| 65a | 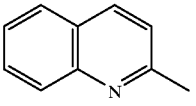 | —CH$_2$O— | 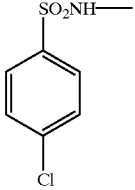 | 4 | 546 (M$^+$)<br>356<br>282 |
| 66a | 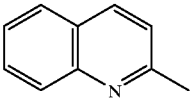 | —CH$_2$CH$_2$— | 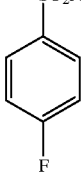 | 4 | 508 (M$^+$)<br>318<br>246 |
| 67a | 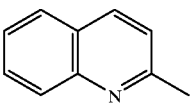 | —CH$_2$CH$_2$— | 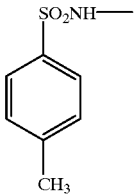 | 4 | 492 (M$^+$)<br>318<br>246 |
| 68a | 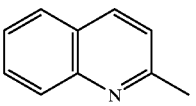 | —CH$_2$CH$_2$— | 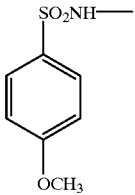 | 4 | 488 (M$^+$)<br>318<br>246 |
| 69a |  | —CH$_2$CH$_2$— |  | 4 | 504 (M$^+$)<br>318<br>246 |

TABLE 1-continued

[Structure: 2-substituted thiazole/imidazole with R1, R2, X positions, connected via A to a meta-substituted phenyl bearing a CH2NH-(CH2)n-R3 group]

For all compounds below, the heterocycle shown is 2-methyl substituted with R1, R2, X:

| Compound No. | (heterocycle) | A | R3 | n | FAB-MS (m/z) |
|---|---|---|---|---|---|
| 70a | 2-methylquinolin-yl | —CH₂CH₂— | 4-Br-C₆H₄-SO₂NH— | 4 | 554 (M⁺), 319, 246 |
| 71a | 2-methylquinolin-yl | —CH₂CH₂— | 4-Cl-C₆H₄-SO₂NH— | 2 | 480 (M⁺), 290, 246 |
| 72a | 2-methylquinolin-yl | —CH₂CH₂— | 4-Cl-C₆H₄-SO₂NH— | 3 | 494 (M⁺), 304, 246 |
| 73a | 2-methylquinolin-yl | —CH₂CH₂— | 4-Cl-C₆H₄-SO₂NH— | 5 | 522 (M⁺), 332, 246 |
| 74a | 7-chloro-2-methylquinolin-yl | —CH₂CH₂— | 4-Cl-C₆H₄-SO₂NH— | 4 | 542 (M⁺), 352, 280 |

TABLE 1-continued
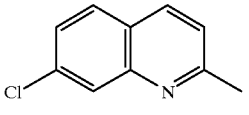
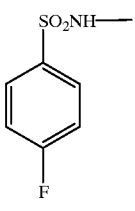
| Compound No. | | A | R3 | n | FAB-MS (m/z) |
|---|---|---|---|---|---|
| 75a | 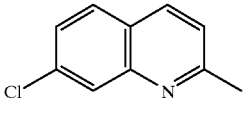 | —CH₂CH₂— | 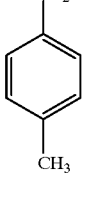 | 4 | 526 (M⁺) 352 280 |
| 76a | 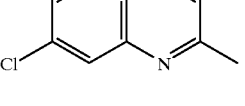 | —CH₂CH₂— | 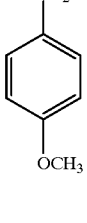 | 4 | 522 (M⁺) 352 280 |
| 77a | 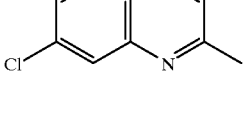 | —CH₂CH₂— | 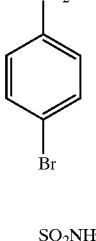 | 4 | 538 (M⁺) 353 280 |
| 78a | 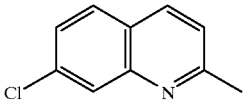 | —CH₂CH₂— | 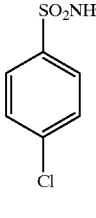 | 4 | 588 (M⁺) 353 280 |
| 79a | | —CH₂CH₂— | | 2 | 515 (M⁺) 325 280 |

TABLE 1-continued
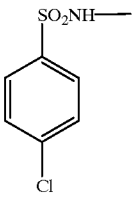
| Compound No. | 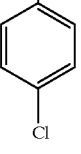 | A | R3 | n | FAB-MS (m/z) |
|---|---|---|---|---|---|
| 80a | 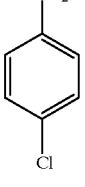 | —CH$_2$CH$_2$— | 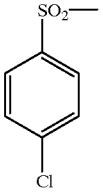 | 3 | 528 (M$^+$) 338 280 |
| 81a | 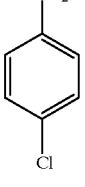 | —CH$_2$O— | 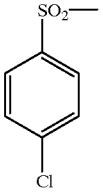 | 5 | 519 (M$^+$) 344 256 |
| 82a | 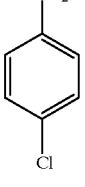 | —CH$_2$O— | 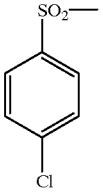 | 5 | 505 (M$^+$) 330 244 |
| 83a | 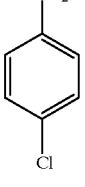 | —CH$_2$O— | 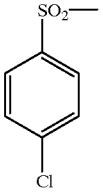 | 5 | 507 (M$^+$) 332 246 |
| 84a | 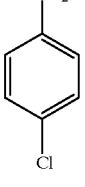 | 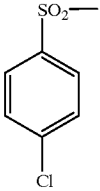 | 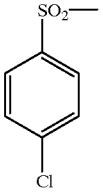 | 5 | 505 (M$^+$) 330 244 |

TABLE 1-continued
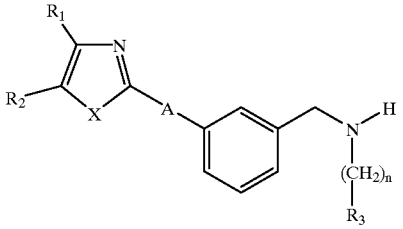
| Compound No. | 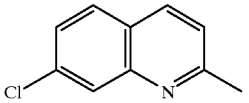 | A | R3 | n | FAB-MS (m/z) |
|---|---|---|---|---|---|
| 85a | 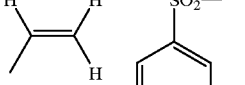 | 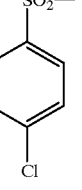 | 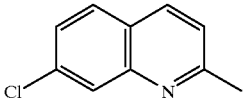 | 5 | 539 (M⁺)<br>364<br>278 |
| 86a | 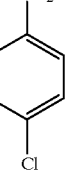 | —CH₂CH₂— | 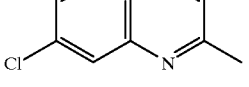 | 5 | 507 (M⁺)<br>332<br>280 |
| 87a | 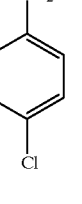 | —CH₂CH₂— | 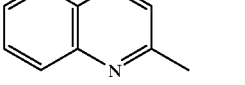 | 5 | 541 (M⁺)<br>366<br>280 |
| 88a | 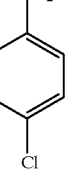 | —CH₂O— | | 5 | 509 (M⁺)<br>334<br>248 |

TABLE 1-continued

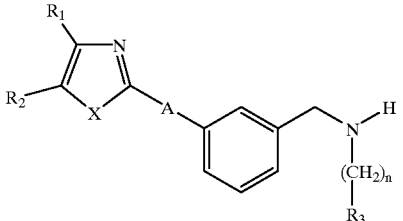

| Compound No. | A | R3 | n | FAB-MS (m/z) |
|---|---|---|---|---|
| 89a | —CH$_2$O— | 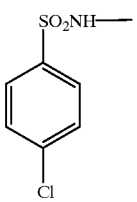 | 4 | 510 (M$^+$) 319 |
| 90a | 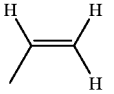 | 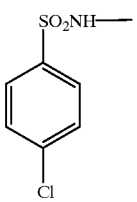 | 4 | 506 (M$^+$) 315 |

Example 10

Preparation of methyl [2-{N-[4-(4-chlorobenzenesulfonylamino)butyl]-N-{3-((4-isopropyl-2-thiazolyl)methoxy]benzyl}}sulfamoylbenzoate (Compound No.1b)

3.5 g (6.89 mmol) of the product in Example 9 (Compound 1a) was dissolved in 150 ml of 1,2-dichloroethane and stirred together with 1.4 ml (10.34 mmol) of triethylamine and 1.9 g (8.27 mmol) of methyl 2-chlorosulfonylbenzoate at room temperature for 4 hours. The 1,2-dichloroethane was distilled off in vacuo, and water and ethyl acetate were added. The ethyl acetate was washed with saturated aqueous sodium chloride, dried over anhydrous magnesium sulfate and evaporated in vacuo for removal of the solvent. The residue was purified by silica gel column chromatography (eluent; chloroform) to give 3.5 g (4.95 mmol) of 2-{N-[4-(4-chlorobenzenesulfonylamino)butyl]-N-{3-[(4-isopropyl-2-thiazolyl)methoxy]benzyl}}sulfamoylbenzoate (Compound No.1b) in a yield of 72%.

Compounds Nos.2b to 90b were prepared similarly. The mass spectrum data are shown in Table 2.

TABLE 2

(wherein R4 is a methyl group)

| Compound No. | R1, R2, X (thiazole) | A | R3 | n | FAB-MS (m/z) |
|---|---|---|---|---|---|
| 1b | 4-isopropyl, 2-methyl thiazole | —CH₂O— | SO₂NH—C₆H₄—Cl (4-Cl) | 4 | 706 (M⁺) 506 |
| 2b | 4-cyclobutyl, 2-methyl thiazole | —CH₂O— | SO₂NH—C₆H₄—F (4-F) | 4 | 702 (M⁺) |
| 3b | 4-cyclobutyl, 2-methyl thiazole | —CH₂O— | SO₂NH—C₆H₄—Br (4-Br) | 4 | 764 (M⁺) 564 |
| 4b | 4-cyclobutyl, 2-methyl thiazole | —CH₂O— | SO₂NH—C₆H₄—OCH₃ (4-OCH₃) | 4 | 714 (M⁺) 514 |
| 5b | 4-cyclobutyl, 2-methyl thiazole | —CH₂O— | SO₂NH—C₆H₄—CH₃ (4-CH₃) | 4 | 698 (M⁺) 498 |

TABLE 2-continued

Structure:
R1, R2 on thiazole (X) connected via A to phenyl-CH2-N(SO2-Ar-COOR4)(CH2)nR3

(wherein R4 is a methyl group)

| Compound No. | [R1/R2/X = 4-cyclobutyl-2-methyl-thiazole] | A | R3 | n | FAB-MS (m/z) |
|---|---|---|---|---|---|
| 6b | 4-cyclobutyl-2-methyl-thiazole | —CH$_2$O— | C$_6$H$_5$-SO$_2$NH— | 4 | 684 (M$^+$) 484 |
| 7b | 4-cyclobutyl-2-methyl-thiazole | —CH$_2$O— | 4-Cl-C$_6$H$_4$-SO$_2$NH— | 3 | 704 (M$^+$) 504 |
| 8b | 4-cyclobutyl-2-methyl-thiazole | —CH$_2$O— | 4-Cl-C$_6$H$_4$-SO$_2$NH— | 2 | 690 (M$^+$) 490 |
| 9b | 4-cyclobutyl-2-methyl-thiazole | —CH$_2$O— | 4-Br-C$_6$H$_4$-SO$_2$NH— | 2 | 734 (M$^+$) 534 |
| 10b | 4-cyclobutyl-2-methyl-thiazole | —CH$_2$O— | 4-F-C$_6$H$_4$-SO$_2$NH— | 2 | 674 (M$^+$) 474 |
| 11b | 4-cyclobutyl-2-methyl-thiazole | —CH$_2$O— | C$_6$H$_5$-SO$_2$NH— | 2 | 656 (M$^+$) 456 |

TABLE 2-continued
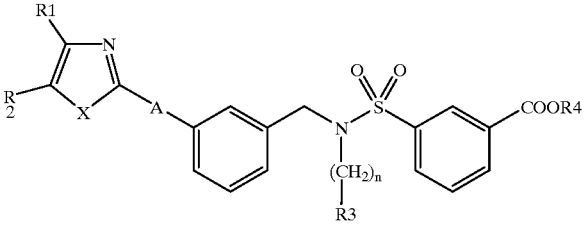
(wherein R4 is a methyl group)
| Compound No. | 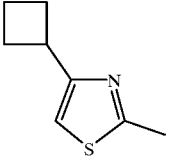 | A | R3 | n | FAB-MS (m/z) |
|---|---|---|---|---|---|
| 12b | 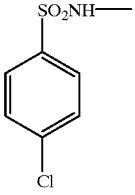 | —CH₂O— | 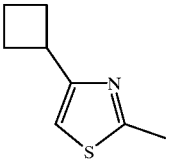 | 5 | 732 (M⁺) 532 |
| 13b | 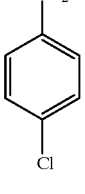 | —CH₂O— | 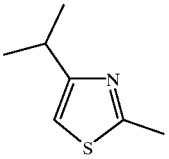 | 4 | 718 (M⁺) 518 |
| 14b | 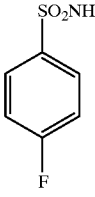 | —CH₂O— | 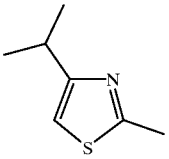 | 4 | 690 (M⁺) 490 |
| 15b | 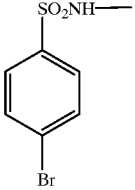 | —CH₂O— | 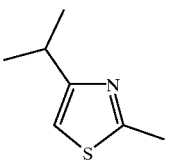 | 4 | 750 (M⁺) 550 |
| 16b | 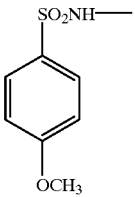 | —CH₂O— | | 4 | 702 (M⁺) 502 |

TABLE 2-continued (structure shown with R1, R2, X on thiazole ring connected via A to phenyl-CH₂-N(SO₂-Ar-COOR4)(CH₂)ₙR3)

(wherein R4 is a methyl group)

| Compound No. | (R1/R2/X thiazole) | A | R3 | n | FAB-MS (m/z) |
|---|---|---|---|---|---|
| 17b | 4-isopropyl-2-methylthiazole | —CH₂O— | 4-methylphenyl-SO₂NH— | 4 | 686 (M⁺) 486 |
| 18b | 4-isopropyl-2-methylthiazole | —CH₂O— | phenyl-SO₂NH— | 4 | 672 (M⁺) 472 |
| 19b | 4-phenyl-2-methylthiazole | —CH₂O— | 4-chlorophenyl-SO₂NH— | 4 | 740 (M⁺) 540 |
| 20b | 4-cyclopropyl-2-methylthiazole | —CH₂O— | 4-chlorophenyl-SO₂NH— | 4 | 704 (M⁺) 504 |
| 21b | 4-cyclopropyl-2-methylthiazole | —CH₂O— | 4-fluorophenyl-SO₂NH— | 4 | 684 (M⁺) 484 |

TABLE 2-continued
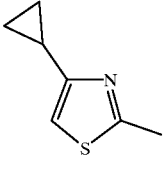
(wherein R4 is a methyl group)
| Compound No. | 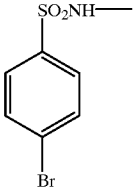 | A | R3 | n | FAB-MS (m/z) |
|---|---|---|---|---|---|
| 22b | 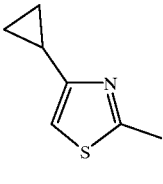 | —CH$_2$O— | 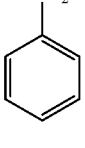 | 4 | 750 (M$^+$) 550 |
| 23b | 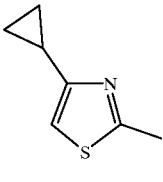 | —CH$_2$O— | 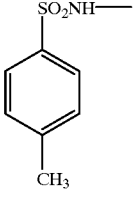 | 4 | 670 (M$^+$) 470 |
| 24b | 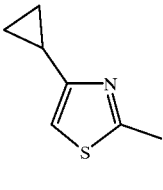 | —CH$_2$O— | 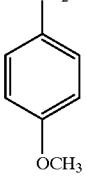 | 4 | 684 (M$^+$) 484 |
| 25b | 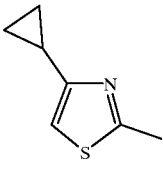 | —CH$_2$O— | 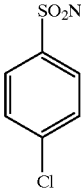 | 4 | 700 (M$^+$) 500 |
| 26b |  | —CH$_2$O— |  | 3 | 690 (M$^+$) 490 |

TABLE 2-continued (wherein R4 is a methyl group)

| Compound No. | ![thiazole with R1, R2, X, 2-methyl] | A | R3 | n | FAB-MS (m/z) |
|---|---|---|---|---|---|
| 27b | 4-cyclopropyl-2-methylthiazole | —CH$_2$O— | SO$_2$NH—(4-Cl-phenyl) | 2 | 676 (M$^+$) 476 |
| 28b | 4-cyclopropyl-2-methylthiazole | —CH$_2$O— | SO$_2$NH—(4-F-phenyl) | 2 | 660 (M$^+$) 460 |
| 29b | 4-cyclobutyl-2-methylthiazole | —CH$_2$CH$_2$— | SO$_2$NH—(4-Cl-phenyl) | 4 | 716 (M$^+$) 516 |
| 30b | 4-cyclobutyl-2-methylthiazole | —CH$_2$CH$_2$— | SO$_2$NH—(4-Br-phenyl) | 4 | 760 (M$^+$) 562 |
| 31b | 4-cyclobutyl-2-methylthiazole | —CH$_2$CH$_2$— | SO$_2$NH—(phenyl) | 4 | 683 (M$^+$) 483 |

TABLE 2-continued

[Structure: R1, R2 substituted thiazole (X)-A-phenyl-CH2-N(SO2-phenyl-COOR4)-(CH2)n-R3]

(wherein R4 is a methyl group)

| Compound No. | R1, R2, X (thiazole) | A | R3 | n | FAB-MS (m/z) |
|---|---|---|---|---|---|
| 32b | 4-cyclobutyl-2-methylthiazole | —CH₂CH₂— | 4-methylphenyl-SO₂NH— | 4 | 697 (M⁺) 497 |
| 33b | 4-isopropyl-2-methylthiazole | —CH₂CH₂— | 4-fluorophenyl-SO₂NH— | 4 | 688 (M⁺) 488 |
| 34b | 4-isopropyl-2-methylthiazole | —CH₂CH₂— | 4-methylphenyl-SO₂NH— | 4 | 685 (M⁺) 485 |
| 35b | 2-methylquinoline | trans-CH=CH-CH₃ | 4-fluorophenyl-SO₂NH— | 4 | 688 (M⁺) 488 |
| 36b | 2-methylquinoline | trans-CH=CH-CH₃ | 4-bromophenyl-SO₂NH— | 4 | 748 (M⁺) 548 |

TABLE 2-continued
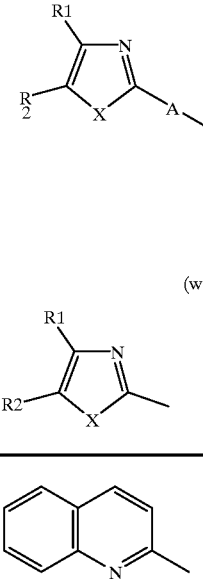
(wherein R4 is a methyl group)
| Compound No. | 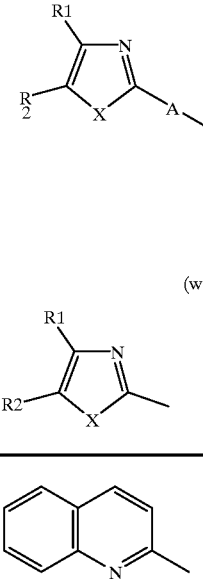 | A | R3 | n | FAB-MS (m/z) |
|---|---|---|---|---|---|
| 37b | | 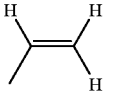 | 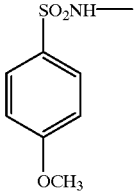 | 4 | 700 (M$^+$) 500 |
| 38b | | 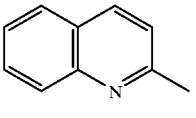 | 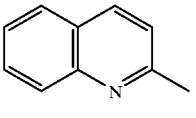 | 4 | 684 (M$^+$) 484 |
| 39b | | 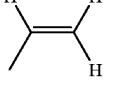 | 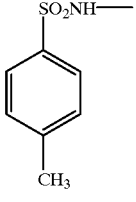 | 4 | 670 (M$^+$) 470 |
| 40b | | 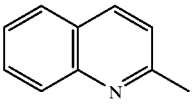 | 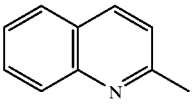 | 3 | 690 (M$^+$) 490 |
| 41b | | 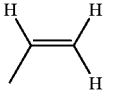 | 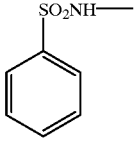 | 2 | 677 (M$^+$) 477 |

TABLE 2-continued
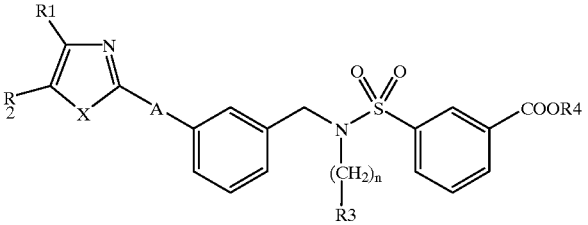
(wherein R4 is a methyl group)
| Compound No. | 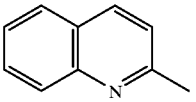 | A | R3 | n | FAB-MS (m/z) |
|---|---|---|---|---|---|
| 42b | | 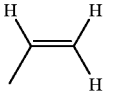 | 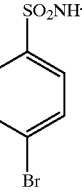 | 2 | 722 (M+) 522 |
| 43b | | 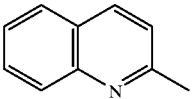 | 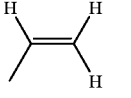 | 2 | 660 (M+) 460 |
| 44b | | 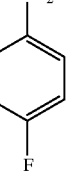 | 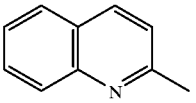 | 2 | 642 (M+) 442 |
| 45b | | 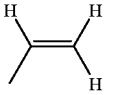 | 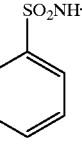 | 4 | 738 (M+) 538 |
| 46b | | 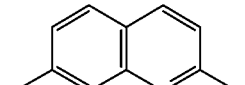 | 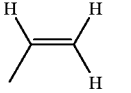 | 4 | 717 (M+) 517 |

TABLE 2-continued (wherein R4 is a methyl group)

| Compound No. | A | R3 | n | FAB-MS (m/z) |
|---|---|---|---|---|
| 47b | 7-chloro-2-methylquinoline | propenyl, 4-bromophenylsulfonamide | 4 | 784 (M⁺) 584 |
| 48b | 7-chloro-2-methylquinoline | propenyl, 4-methoxyphenylsulfonamide | 4 | 734 (M⁺) 534 |
| 49b | 7-chloro-2-methylquinoline | propenyl, 4-methylphenylsulfonamide | 4 | 718 (M⁺) 518 |
| 50b | 7-chloro-2-methylquinoline | propenyl, phenylsulfonamide | 4 | 704 (M⁺) 504 |
| 51b | 7-chloro-2-methylquinoline | propenyl, 4-chlorophenylsulfonamide | 3 | 724 (M⁺) 524 |

TABLE 2-continued (Structure with R1, R2, X, A, N-SO2, (CH2)n-R3, COOR4 substituents shown)

(wherein R4 is a methyl group)

| Compound No. | (R1, R2, X with 2-methyl) | A | R3 | n | FAB-MS (m/z) |
|---|---|---|---|---|---|
| 52b | 7-chloro-2-methylquinoline | CH=CH (cis) | 4-chlorophenyl-SO2NH— | 2 | 710 (M+) 510 |
| 53b | 2-methylquinoline | —CH2O— | 4-fluorophenyl-SO2NH— | 4 | 692 (M+) 492 |
| 54b | 2-methylquinoline | —CH2O— | 4-bromophenyl-SO2NH— | 4 | 753 (M+) 553 |
| 55b | 2-methylquinoline | —CH2O— | 4-methoxyphenyl-SO2NH— | 4 | 704 (M+) 504 |
| 56b | 2-methylquinoline | —CH2O— | 4-methylphenyl-SO2NH— | 4 | 688 (M+) 488 |

TABLE 2-continued (structure shown: R1, R2 on thiazole (X) ring connected via A to phenyl-CH2-N(SO2-C6H4-COOR4)-(CH2)n-R3)

(wherein R4 is a methyl group)

| Compound No. | R1/R2/X (2-methylthiazole shown) | A | R3 | n | FAB-MS (m/z) |
|---|---|---|---|---|---|
| 57b | 2-methylquinoline | —CH2O— | SO2NH—phenyl | 4 | 674 (M+) 474 |
| 58b | 2-methylquinoline | —CH2O— | SO2NH—(4-Cl-phenyl) | 3 | 688 (M+) 488 |
| 59b | 2-methylquinoline | —CH2O— | SO2NH—(4-Cl-phenyl) | 2 | 680 (M+) 480 |
| 60b | 2-methylquinoline | —CH2O— | SO2NH—(4-F-phenyl) | 2 | 664 (M+) 464 |
| 61b | 2-methylquinoline | —CH2O— | SO2NH—(4-Br-phenyl) | 2 | 724 (M+) 524 |
| 62b | 2-methylquinoline | —CH2O— | SO2NH—phenyl | 2 | 657 (M+) 457 |

TABLE 2-continued
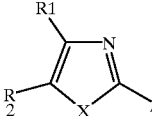
(wherein R4 is a methyl group)
| Compound No. | 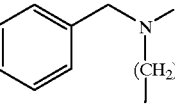 | A | R3 | n | FAB-MS (m/z) |
|---|---|---|---|---|---|
| 63b | 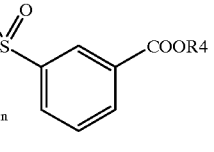 | —CH₂O— | 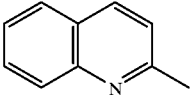 | 5 | 735 (M⁺) 535 |
| 64b |  | —CH₂O— | 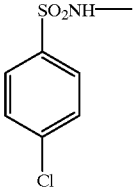 | 2 | 714 (M⁺) 514 |
| 65b |  | —CH₂O— | 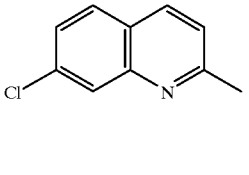 | 4 | 744 (M⁺) 544 |
| 66b |  | —CH₂CH₂— | 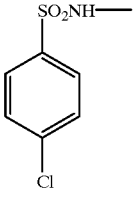 | 4 | 706 (M⁺) 506 |
| 67b |  | —CH₂CH₂— | 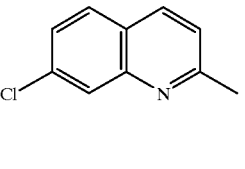 | 4 | 690 (M⁺) 490 |

TABLE 2-continued

[Structure: R1, R2 on thiazole (X) connected to A-phenyl-CH2-N(SO2-phenyl-COOR4)(CH2)n-R3]

(wherein R4 is a methyl group)

| Compound No. | [R1, R2, X thiazole with 2-methyl] | A | R3 | n | FAB-MS (m/z) |
|---|---|---|---|---|---|
| 68b | 2-methylquinolin-yl | —CH2CH2— | 4-methylphenyl-SO2NH— | 4 | 686 (M+) 486 |
| 69b | 2-methylquinolin-yl | —CH2CH2— | 4-methoxyphenyl-SO2NH— | 4 | 702 (M+) 502 |
| 70b | 2-methylquinolin-yl | —CH2CH2— | 4-bromophenyl-SO2NH— | 4 | 752 (M+) 552 |
| 71b | 2-methylquinolin-yl | —CH2CH2— | 4-chlorophenyl-SO2NH— | 2 | 678 (M+) 478 |
| 72b | 2-methylquinolin-yl | —CH2CH2— | 4-chlorophenyl-SO2NH— | 3 | 692 (M+) 492 |

TABLE 2-continued
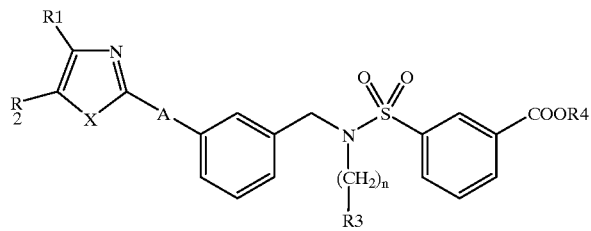
(wherein R4 is a methyl group)
| Compound No. | [R1/R2/X core] | A | R3 | n | FAB-MS (m/z) |
|---|---|---|---|---|---|
| 73b | 2-methyl-quinoline | —CH₂CH₂— | 4-Cl-C₆H₄-SO₂NH— | 5 | 720 (M⁺) 520 |
| 74b | 7-chloro-2-methyl-quinoline | —CH₂CH₂— | 4-Cl-C₆H₄-SO₂NH— | 4 | 740 (M⁺) 540 |
| 75b | 7-chloro-2-methyl-quinoline | —CH₂CH₂— | 4-F-C₆H₄-SO₂NH— | 4 | 724 (M⁺) 524 |
| 76b | 7-chloro-2-methyl-quinoline | —CH₂CH₂— | 4-CH₃-C₆H₄-SO₂NH— | 4 | 720 (M⁺) 520 |
| 77b | 7-chloro-2-methyl-quinoline | —CH₂CH₂— | 4-OCH₃-C₆H₄-SO₂NH— | 4 | 736 (M⁺) 536 |

TABLE 2-continued (structure shown with R1, R2, X, A, phenyl, N-SO2-phenyl-COOR4, (CH2)n, R3)

(wherein R4 is a methyl group)

| Compound No. | R1/R2/X (ring) | A | R3 | n | FAB-MS (m/z) |
|---|---|---|---|---|---|
| 78b | 7-chloro-2-methylquinoline | —CH₂CH₂— | SO₂NH—(4-Br-phenyl) | 4 | 786 (M⁺) 586 |
| 79b | 7-chloro-2-methylquinoline | —CH₂CH₂— | SO₂NH—(4-Cl-phenyl) | 2 | 713 (M⁺) 513 |
| 80b | 7-chloro-2-methylquinoline | —CH₂CH₂— | SO₂NH—(4-Cl-phenyl) | 3 | 726 (M⁺) 526 |
| 81b | 4-cyclobutyl-2-methylthiazole | —CH₂O— | SO₂—(4-Cl-phenyl) | 5 | 717 (M⁺) 517 |
| 82b | 4-cyclopropyl-2-methylthiazole | —CH₂O— | SO₂—(4-Cl-phenyl) | 5 | 703 (M⁺) 503 |

TABLE 2-continued
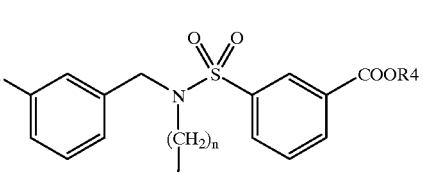
(wherein R4 is a methyl group)
| Compound No. | 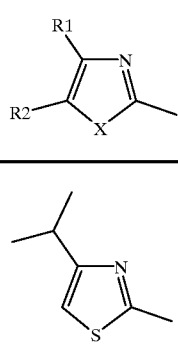 | A | R3 | n | FAB-MS (m/z) |
|---|---|---|---|---|---|
| 83b | 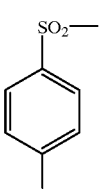 | —CH$_2$O— | 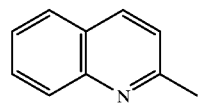 | 5 | 705 (M$^+$) 505 |
| 84b | 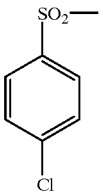 | 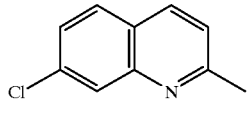 | 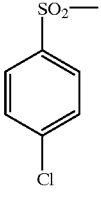 | 5 | 703 (M$^+$) 503 |
| 85b | 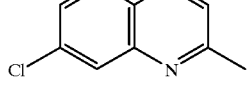 | 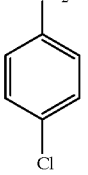 | 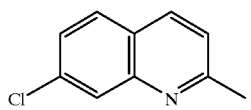 | 5 | 737 (M$^+$) 537 |
| 86b | 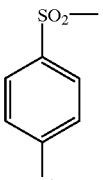 | —CH$_2$CH$_2$— | 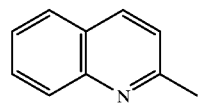 | 5 | 705 (M$^+$) 505 |
| 87b | 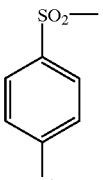 | —CH$_2$CH$_2$— | 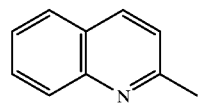 | 5 | 739 (M$^+$) 539 |

TABLE 2-continued

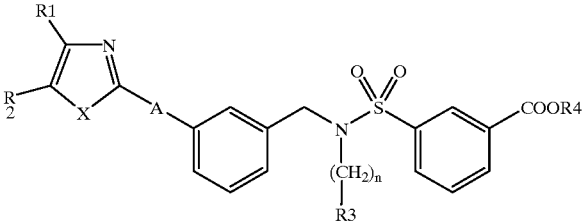

Example 11

Preparation of 2-{N-[4-(4-chlorobenzenesulfonylamino)butyl]-N-{3-[(4-isopropyl-2-thiazolyl)methoxy]benzyl}}sulfamoylbenzoic acid (Compound No.1)

3.2 g (4.53 mmol) of the product in Example 10 (Compound No.1b) was dissolved in 70 ml of methanol and 70 ml of tetrahydrofuran and stirred together with 50 ml of 1N sodium hydroxide at 80° C. for 3 hours. The reaction solution was evaporated in vacuo for removal of the solvent, mixed with water and neutralized with 1N hydrochloric acid, and the deposited precipitate was filtered off to give 2.7 g (3.9 mmol) of the title compound (Compound No.1) in a yield of 86%.

Compounds Nos.2 to 90 were prepared similarly. The mass spectrum data are shown in Table 3.

TABLE 3

| Compound No. | R1, R2, X (ring) | A | R3 | n | Physicochemical properties |
|---|---|---|---|---|---|
| 1 | 4-isopropyl-2-methyl-thiazole | —CH₂O— | 4-Cl-C₆H₄-SO₂NH— | 4 | FAB-MS: (m/z)692(M⁺)508 458 246<br>¹H NMR(CDCl₃)<br>1.31(10H, m)2.75(2H, br s)3.15(2H, t J=6.8Hz)4.40(2H, s)5.33(2H, s)<br>6.81–6.91(4H, m)7.15(1H, t J=7.8Hz)<br>7.38(2H, d J=7.38Hz)7.51–7.64(3H, m)<br>7.71(2H, d J=8.58Hz)7.90(1H, d J=7.26Hz) |
| 2 | 4-cyclobutyl-2-methyl-thiazole | —CH₂O— | 4-F-C₆H₄-SO₂NH— | 4 | FAB-MS: (m/z)688(M⁺)504 346 258<br>¹H NMR(CDCl₃)<br>1.33(4H, m)1.88–2.12(2H, m)2.17–2.43(4H, m)2.75(2H, br s)3.14(2H, br t)3.72(1H, quint)4.40(2H, s)5.12(1H, br s)5.37(2H, s)6.81–6.90(2H, m)6.95(1H, d J=0.7Hz)7.08–7.14(3H, m)7.54–7.68(3H, m)7.80(2H, m)7.94(1H, d J=7.59Hz) |
| 3 | 4-cyclobutyl-2-methyl-thiazole | —CH₂O— | 4-Br-C₆H₄-SO₂NH— | 4 | FAB-MS: (m/z)750(M⁺+1)670 564<br>¹H NMR(CDCl₃)<br>1.26(4H, m)1.87–2.10(2H, m)2.06–2.40(4H, m)2.71(2H, br s)3.13(2H, br s)3.65(1H, quint)4.38(2H, s)5.28(2H, s)5.68(1H, br s)6.83(2H, m)6.92(1H, s)7.14(1H, t J=7.9Hz)7.45–7.50(5H, m)7.61(2H, d J=8.58Hz)7.82(1H, d J=7.59Hz) |
| 4 | 4-cyclobutyl-2-methyl-thiazole | —CH₂O— | 4-OCH₃-C₆H₄-SO₂NH— | 4 | FAB-MS: (m/z)700(M⁺)516 365 240<br>¹H NMR(CDCl₃)<br>1.26(4H, m)1.83–2.09(2H, m)2.1–2.36(4H, m)3.11(2H, br s)3.67(1H, quint)3.79(3H, s)4.35(2H, br s)5.26(2H, br s)6.72–7.09(5H, m)7.12(1H, br s)7.26(1H, s)7.30–7.90(6H, m) |
| 5 | 4-cyclobutyl-2-methyl-thiazole | —CH₂O— | 4-CH₃-C₆H₄-SO₂NH— | 4 | FAB-MS: (m/z)684(M⁺)645 500<br>¹H NMR(CDCl₃)<br>1.22–1.32(4H, m)1.86–2.10(2H, m)2.16–2.31(4H, m)2.36(3H, s)2.71(2H, br s)3.13(2H, br s)3.72(1H, quint)4.38(2H, 2)5.29(2H, s)6.81–6.92(4H, m)7.10–7.21(3H, m)7.44–7.59(3H, m)7.65(2H, d J=8.25Hz)7.87(1H, d J=7.59Hz) |

TABLE 3-continued

| Compound No. | R1, R2, X (thiazole) | A | R3 | n | Physicochemical properties |
|---|---|---|---|---|---|
| 6 | 4-cyclobutyl-2-methylthiazole | —CH₂O— | SO₂NH-phenyl | 4 | FAB-MS: (m/z)670(M⁺)486 346<br>¹H NMR(CDCl₃)<br>1.23–1.34(4H, m)1.91–2.16(2H, m)2.19–2.42(4H, m)2.73(2H, br s)3.13(2H, br s)3.71(1H, quint)4.39(2H, s)5.11(1H, br s)5.34(2H, s)6.81–6.94(4H, m)7.13(1H, t J=7.76Hz)7.41–7.65(6H, m)7.78(2H, d J=6.93Hz)7.92(1H, d J=7.59Hz) |
| 7 | 4-cyclobutyl-2-methylthiazole | —CH₂O— | SO₂NH-(4-Cl-phenyl) | 3 | FAB-MS: (m/z)690(M⁺)346 258<br>¹H NMR(CDCl₃)<br>1.41(2H, br s)1.92–2.12(2H, m)2.20–2.42(4H, m)2.73(2H, br s)3.22(2H, br s)3.70(1H, quint)4.38(2H, s)5.33(2H, s)5.74(1H, br s)6.80–6.94(4H, m)7.14(1H, t)7.35(2H, d J=8.58Hz)7.52–7.60(3H, m)7.69-(2H, d J=8.57Hz, 7.85(1H, d J=7.26Hz) |
| 8 | 4-cyclobutyl-2-methylthiazole | —CH₂O— | SO₂NH-(4-Cl-phenyl) | 2 | FAB-MS: (m/z)676(M⁺)492 458<br>¹H NMR(CDCl₃)<br>1.92–2.40(6H, m)2.70(2H, br s)3.26(2H, br s)3.71(1H, m)4.34(2H, s)5.40(2H, s)6.19(1H, br s)6.77–6.97(4H, m)7.12(1H, m)7.25–7.31(3H, m)7.50–7.62(5H, m)7.93(1H, d) |
| 9 | 4-cyclobutyl-2-methylthiazole | —CH₂O— | SO₂NH-(4-Br-phenyl) | 2 | FAB-MS: (m/z)720(M⁺)642 536<br>¹H NMR(CDCl₃)<br>1.85–2.13(2H, m)2.15–2.44(4H, m)2.70(2H br s)3.27(2H, t J=5.6Hz)4.34(2H, s)5.42(2H, s)6.16(1H, br s)6.77(1H, d J=7.91Hz)6.87–6.90(2H, m)6.97(1H, s)7.42–7.63(7H, m)7.95(1H, d J=7.59Hz) |
| 10 | 4-cyclobutyl-2-methylthiazole | —CH₂O— | SO₂NH-(4-F-phenyl) | 2 | FAB-MS: (m/z)660(M⁺)476 258<br>¹H NMR(CDCl₃)<br>1.85–2.43(4H, m)2.71(2H, br s)3.25(2H, m)3.74(1H, quint)4.33(2H, s)5.46(2H, s)5.97(1H, br s)6.77(1H, d J=7.58Hz)6.85–6.92(2H, m)6.98–7.15(4H, m)7.54–7.69(5H, m)8.00(1H, d J=7.58Hz) |

TABLE 3-continued

| Compound No. | R1, R2, X (structure) | A | R3 | n | Physicochemical properties |
|---|---|---|---|---|---|
| 11 | cyclobutyl-thiazole-methyl | —CH₂O— | SO₂NH-phenyl | 2 | FAB-MS: (m/z)642(M⁺)458<br>¹H NMR(CDCl₃)<br>1.89–2.43(6H, m)2.73(2H, br s)3.25<br>(2H, m)3.74(1H, quint)4.31(2H, s)<br>5.43(2H, s)5.89(1H, br s)6.77(1H, d<br>J=7.58Hz)6.89(2H, m)6.97(1H, d J=0.66<br>Hz)7.11(1H, t J=7.92Hz)7.35–7.70<br>70(3H, m)8.00(1H, d J=7.58Hz) |
| 12 | cyclobutyl-thiazole-methyl | —CH₂O— | SO₂NH-phenyl-Cl | 5 | FAB-MS: (m/z)718(M⁺) 684 645 534<br>¹H NMR(CDCl₃)<br>1.05(2H, m)1.27(4H, m)1.85–2.45(6H, m)<br>2.78(2H, m)3.10(2H, m)3.73(1H, quint)<br>4.40(2H, s)5.13(1H, br s)5.37<br>(2H, s)6.82–6.90(2H, m)6.95(2H, d<br>J=0.66Hz)7.16(1H, m)7.46(2H, m)7.54–<br>7.74(3H, m)7.76(2H, dd J=1.98 6.93Hz)<br>7.96(1H, m) |
| 13 | cyclobutyl-thiazole-methyl | —CH₂O— | SO₂NH-phenyl-Cl | 4 | FAB-MS: (m/z)704(M⁺)520<br>¹H NMR(CDCl₃)<br>1.30(4H, m)1.90–2.08(2H, m)2.16–2.39<br>(4H, m)2.72(2H, br s)3.14(2H, br s)<br>3.71(1H, quint)4.40(2H, s)5.22(1H, br s)<br>5.36(2H, s)6.80–6.94(4H, m)7.13(1H,<br>d J=7.59Hz)7.38(2H, d J=6.92Hz)<br>7.54–7.72(5H, m)7.89(1H, d) |
| 14 | isopropyl-thiazole-methyl | —CH₂O— | SO₂NH-phenyl-F | 4 | FAB-MS: (m/z)676(M⁺)492 228<br>¹H NMR(CDCl₃)<br>1.31(10H, m)2.77(2H,3.14(3H, m)<br>4.43(2H, s)5.14(1H, t J=5.78Hz)5.37<br>(2H, s)6.81–6.95(4H, m)7.08–7.18<br>(3H, m)7.53–7.70(3H, m)7.81–7.92(2H, m)<br>7.94(1H, d J=7.59Hz) |
| 15 | isopropyl-thiazole-methyl | —CH₂O— | SO₂NH-phenyl-Br | 4 | FAB-MS: (m/z)736(M⁺)552 246<br>¹H NMR(CDCl₃)<br>1.31(10H, m)2.74(2H, m)3.14(3H, m)<br>4.41(2H, s)5.35(2H, s)5.25(1H, br S)<br>6.81–6.92(4H, m)7.14(1H, t J=7.92Hz)<br>7.51–7.81(7H, m)7.90(1H, m) |

TABLE 3-continued

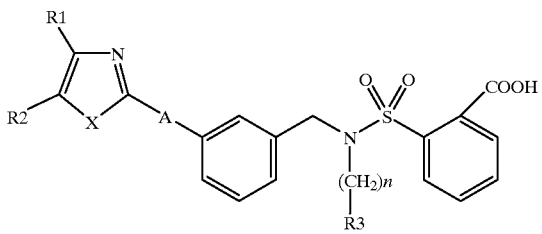

| Compound No. | R1, R2, X (thiazole) | A | R3 | n | Physicochemical properties |
|---|---|---|---|---|---|
| 16 | 4-isopropyl-2-methyl thiazole | —CH₂O— | SO₂NH—C₆H₄—OCH₃ (para) | 4 | FAB-MS: (m/z)688(M⁺)504<br>¹H NMR(CDCl₃)<br>1.24–1.33(10H, m)2.73(2H, m)3.10–3.23(3H, m)3.84(3H, s)4.39(2H, s)4.64(1H, br s)4.92(1H, br s)5.36(2H, s)6.82–6.94(6H, m)7.15(1H, t J=7.92Hz)7.53–7.74(5H, m)7.95(1H, d J=7.59Hz) |
| 17 | 4-isopropyl-2-methyl thiazole | —CH₂O— | SO₂NH—C₆H₄—CH₃ (para) | 4 | FAB-MS: (m/z)672(M⁺)488 334 246<br>¹H NMR(CDCl₃)<br>1.09–1.33(10H, m)2.39(3H, s)2.72(2H, m)3.11–3.22(3H, m)4.40(1H, br s)4.97(1H, br s)5.36(2H, s)5.59(1H, br s)6.82–6.93(4H, m)7.14(1H, t J=7.92Hz)7.25(2H, d J=8.24Hz)7.52–7.68(4H, m)7.94(1H, d J=7.26Hz) |
| 18 | 4-isopropyl-2-methyl thiazole | —CH₂O— | SO₂NH—C₆H₅ | 4 | FAB-MS: (m/z)658(M⁺)518 474<br>¹H NMR(CDCl₃)<br>1.25–1.33(10H, m)2.76(2H, m)3.11–3.18(3H, m)4.40(2H, s)5.13(1H, br s)5.34(2H, s)6.82–6.93(4H, m)7.15(1H, t J=7.92Hz)7.43–7.67(6H, m)7.79(2H, d J=6.93Hz)7.93(1H, d J=7.59Hz) |
| 19 | 4-phenyl-2-methyl thiazole | —CH₂O— | SO₂NH—C₆H₄—Cl (para) | 4 | FAB-MS: (m/z)726(M⁺)542<br>¹H NMR(CDCl₃)<br>1.25–1.33(4H, m)2.72(2H, br s)3.17(2H, m)4.39(2H, s)5.33(2H, s)6.82–6.91(3H, m)7.16(1H, m)7.30–7.58(10H, m)7.69(2H, dd J=6.75 1.8Hz)7.83–7.87(3H, m) |
| 20 | 4-cyclopropyl-2-methyl thiazole | —CH₂O— | SO₂NH—C₆H₄—Cl (para) | 4 | FAB-MS: (m/z)690(M⁺)504<br>¹H NMR(CDCl₃)<br>0.85–0.93(4H, m)1.13(4H, d J=6.26Hz)2.05(1H, br s)2.68(2H, br s)3.13(2H, br s)4.38(2H, s)5.23(2H, s)6.70–6.90(3H, m)7.13(1H, br s)7.30–7.90(8H, m) |

TABLE 3-continued

[Structure: R1-R2-X-thiazole-A-phenyl-CH2-N(SO2-phenyl-COOH)(CH2)n-R3]

| Compound No. | R1/R2/X (thiazole) | A | R3 | n | Physicochemical properties |
|---|---|---|---|---|---|
| 21 | 4-cyclopropyl-2-methyl-thiazole | —CH$_2$O— | SO$_2$NH—(4-F-phenyl) | 4 | FAB-MS: (m/z)674(M$^+$)490 353 244<br>$^1$H NMR(CDCl$_3$)<br>0.82–0.99(4H, m)1.13(4H, d J=6.26Hz)<br>2.08(1H, m)2.75(2H, br s)3.12(2H, m)4.40(2H, s)5.23(1H, br s)6.81–6.89(4H, m)7.07–7.17(3H, m)7.51–7.66(3H, m)7.77–7.82(2H, m)7.90(1H, d J=7.26Hz) |
| 22 | 4-cyclopropyl-2-methyl-thiazole | —CH$_2$O— | SO$_2$NH—(4-Br-phenyl) | 4 | FAB-MS: (m/z)736(M$^+$+1)550 244 246<br>$^1$H NMR(CDCl$_3$)<br>0.80–0.95(4H, m)1.18–1.23(4H, m)2.23(1H, m)2.62(2H, br s)3.06(2H, br s)4.33(2H, s)5.17(2H, s)6.88(4H, br s)7.12(1H, m)7.26–7.47(6H, m)77.56(2H, d J=8.58Hz)7.63(1H, d J=7.92Hz) |
| 23 | 4-cyclopropyl-2-methyl-thiazole | —CH$_2$O— | SO$_2$NH—phenyl | 4 | FAB-MS: (M/Z)656(M$^+$)472 332<br>$^1$H NMR(CDCl$_3$)<br>0.86–0.96(4H, m)1.25(4H, m)2.09(3H, m)2.76(2H, br s)3.15(2H, br s)4.39 2H, s)5.29(2H, s)6.83–6.90(4H, m) 7.14(1H, m)7.46–7.66(6H, m)7.80(2H, d J=7.26Hz)7.93(1H, d J=7.26Hz) |
| 24 | 4-cyclopropyl-2-methyl-thiazole | —CH$_2$O— | SO$_2$NH—(4-CH$_3$-phenyl) | 4 | FAB-MS(m/z)670(M$^+$)486 349 244<br>$^1$H NMR(CDCl$_3$)<br>0.81–0.94(4H, m)1.24–1.32(4H, m)2.02–2.12(1H, m)2.37(3H, s)2.73(2H, br s)3.15(2H, m)4.39(2H, s)5.25(2H, s)6.82–6.87(4H, m)7.11–7.26(4H, m)7.47–7.67(5H, m)7.87(1H, d J=7.26Hz) |
| 25 | 4-cyclopropyl-2-methyl-thiazole | —CH$_2$O— | SO$_2$NH—(4-OCH$_3$-phenyl) | 4 | FAB-MS: (m/z)686(M$^+$)<br>$^1$H NMR(CDCl$_3$)<br>0.84–0.99(4H, m)1.25–1.36(4H, m)2.09(1H, m)2.74(2H, br s)3.15(2H, d J=6.93Hz)3.84(3H, s)4.39(2H, s)5.01(1H, br s)5.29(2H, s)6.82–6.94(6H m)7.15(1H, t J=7.92Hz)7.52–7.75(5H, m)7.93(1H, d J=7.59Hz) |

TABLE 3-continued

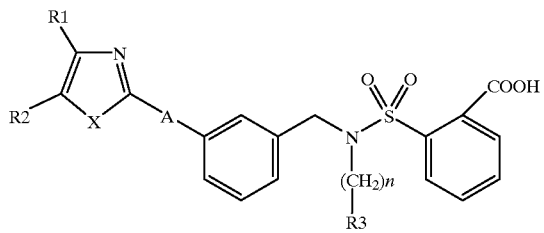

| Compound No. | 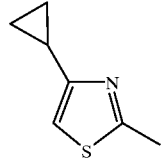 | A | R3 | n | Physicochemical properties |
|---|---|---|---|---|---|
| 26 | 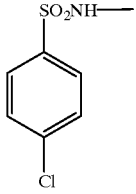 | —CH₂O— | 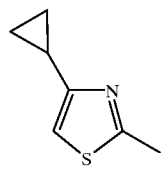 | 3 | FAB-MS: (m/z)676(M⁺)493 318 244<br>¹H NMR(CDCl₃)<br>0.82–0.99(4H, m)1.40(2H, d J=5.94Hz)<br>2.08(1H, m)2.77(2H, br s)3.26(2H, m)4.38(2H, s)5.28(1H, s)5.66(1H, br s)6.80–6.88(4H, m)7.15(1H, m)7.39 (2H, dd J=6.92 1.98Hz)7.52–7.63 (3H, m)7.71(2H, dd J=6.93 1.98Hz)7.86 (1H d J=7.26Hz) |
| 27 | 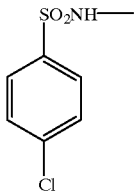 | —CH₂O— | 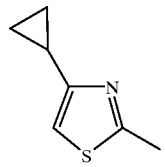 | 2 | FAB-MS: (m/z)662(M⁺)478 341<br>¹H NMR(CDCl₃)<br>0.82–0.98(4H, m)2.09(1H, m)2.73(2H, br s)3.30(2H, t J=5.75Hz)4.35(2H, s)5.36(2H, s)6.02(1H, br s)6.78–6.91(4H, m)7.13(1H, t J=7.76Hz)7.33 (2H, d J=8.58Hz)7.53–7.67(5H, m)7.96 (1H, d J=7.59Hz) |
| 28 | 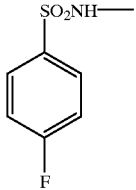 | —CH₂O— | 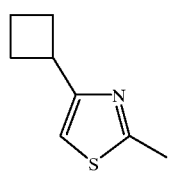 | 2 | FAB-MS: (m/z)646(M⁺)<br>¹H NMR(CDCl₃)<br>0.82–0.97(4H, m)2.09(1H, m)2.74(2H, br s)3.30(2H, t J=5.78Hz)4.35(2H, s)5.34(2H, s)5.94(1H, br s)6.78–6.89(4H, m)7.00–7.16(3H, m)7.53–7.65 (5H, m)7.95(1H, d J=7.92Hz) |
| 29 | 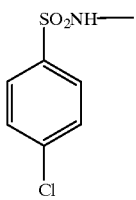 | —CH₂CH₂— | 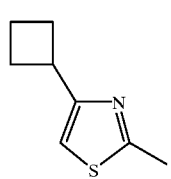 | 4 | FAB-MS: (m/z)702(M⁺)518 256 244<br>¹H NMR(CDCl₃)<br>1.20–1.40(4H, m)1.82–2.41(6H, m)2.75 (2H, br s)3.01(2H, t)3.14(2H, t) 3.31(2H, t)3.66(1H, quint)4.39(2H, s)5.38(1H, br s)6.77(1H, s)7.02–7.17 (4H, m)7.50–7.65(3H, m)7.71(2H, d J=8.58Hz)7.38(2H, d J=8.57Hz)7.90 (1H, d J=7.26Hz) |
| 30 | 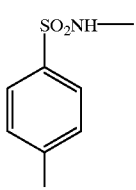 | —CH₂CH₂— | 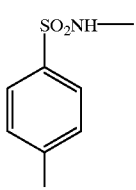 | 4 | FAB-MS: (m/z)748(M⁺)670 564<br>¹H NMR(CDCl₃)<br>1.20–1.40(4H, m)1.81–2.41(6H, m)2.73 (2H, br s)3.03(2H, m)3.13(2H, m) 3.32(2H, m)3.66(1H, quint)4.39(2H, s)5.38(1H, br s)6.77(1H, s)7.02–7.16(5H, m)7.52–7.65(6H, m)7.89(1H, d J=7.59Hz) |

TABLE 3-continued

| Compound No. | R1, R2, X (thiazole structure) | A | R3 | n | Physicochemical properties |
|---|---|---|---|---|---|
| 31 | 4-cyclobutyl-2-methylthiazole | —CH₂CH₂— | SO₂NH-phenyl | 4 | FAB-MS: (m/z)669(M⁺)<br>¹H NMR(CDCl₃)<br>0.82–0.99(4H, m)1.40(2H, d J=5.94Hz)<br>2.08(1H, m)2.77(2H, br s)3.26(2H, m)4.38(2H, s)5.28(1H, s)5.66(1H, br s)6.80–6.88(4H, m)7.15(1H, m)7.39 (2H, dd J=6.92 1.98Hz)7.52–7.63 (3H, m)7.71(2H, dd J=6.93 1.98Hz)7.86 (1H d J=7.26Hz) |
| 32 | 4-cyclobutyl-2-methylthiazole | —CH₂CH₂— | SO₂NH-(4-methylphenyl) | 4 | FAB-MS: (m/z)683(M⁺)<br>¹H NMR(CDCl₃)<br>1.20–1.40(4H, m)1.82–2.37(6H, m)2.39 (3H, m)2.72(2H, m)3.01(2H, t)3.13 (2H, t)3.33(2H, t)3.67(1H, quint) 4.38(2H, s)6.76(1H, d J=0.66Hz)7.04– 7.26(7H, m)7.51–7.68(4H, m)7.92(1H, d J=7.59Hz) |
| 33 | 4-isopropyl-2-methylthiazole | —CH₂CH₂— | SO₂NH-(4-fluorophenyl) | 4 | FAB-MS: (m/z)674(M⁺)<br>¹H NMR(CDCl₃)<br>1.28(10H, m)2.70–2.78(2H, m)2.99–3.66 (4H, m)3.34(2H, m)4.39(2H, s)5.21 (1H, br t)6.74(1H, s)7.16(6H, m) .52–7.67(3H, m)7.77–7.82(2H, m) 7.91(1H, d J=7.59Hz) |
| 34 | 4-isopropyl-2-methylthiazole | —CH₂CH₂— | SO₂NH-(4-methylphenyl) | 4 | FAB-MS: (m/z)671(M⁺)<br>¹H NMR(CDCl₃)<br>1.28(10H, m)2.39(3H, s)2.68(2H, m) 2.99–3.19(4H, m)3.34(2H, m)4.38(2H, s) 5.00(1H, br t)6.73(1H, s)7.03– 7.26(6H, m)7.51–7.68(5H, m)7.92(1H, d J=7.26Hz) |
| 35 | 2-methylquinoline | trans-CH=C(CH₃)— | SO₂NH-(4-fluorophenyl) | 4 | FAB-MS(m/z)674(M⁺)645<br>¹H NMR(CDCl₃)<br>1.23–1.35(4H, m)2.65(2H, br s)3.20 (2H, br s)4.52(2H, s)5.77(1H, br s) 6.81–7.05(3H, m)7.15–7.17(2H, m) 7.39–7.95(13H, m)8.25(2H, m) |

TABLE 3-continued

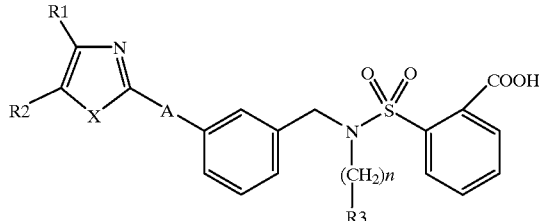

| Compound No. | 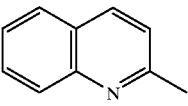 | A | R3 | n | Physicochemical properties |
|---|---|---|---|---|---|
| 36 | 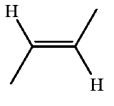 | 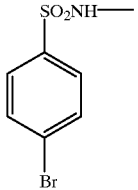 | 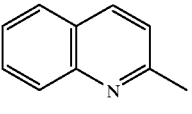 | 4 | FAB-MS: (m/z)734(M⁺)550 244<br>¹H NMR(CDCl₃)<br>1.22–1.33(4H, m)2.63(2H, br s)3.19<br>(2H, br s)4.52(2H, s)5.96(1H, br s)<br>7.05–7.16(2H, m)7.38–7.93(16H, m)<br>8.25(2H, m) |
| 37 | 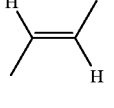 | 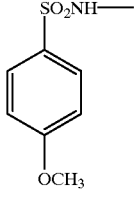 | 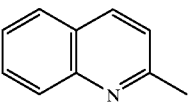 | 4 | FAB-MS: (m/z)686(M⁺)645<br>¹H NMR(CDCl₃)<br>1.22–1.35(4H, m)2.66(2H, br s)3.21<br>(2H, br s)3.77(3H, s)4.52(2H, s)5.29<br>(1H, br s)6.82(2H, m)5.29(1H, br s)<br>6.82(2H, m)7.19(2H, d J=4.62Hz)<br>7.40–7.94(14H, m)8.25(2H, s) |
| 38 | 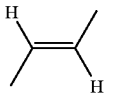 | 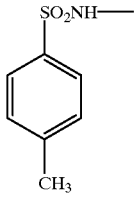 | 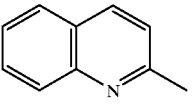 | 4 | FAB-MS: (m/z)670(M⁺) 645 553<br>¹H NMR(CDCl₃)<br>1.19–1.32(4H, m)2.31(3H, s)2.63(2H,<br>br s)3.19(2H, br s)4.50(2H, s)5.44<br>(1H, br s)7.26(4H, m)7.39–7.78(13H,<br>m)7.87(1H, d J=7.92Hz)8.24(2H, m) |
| 39 | 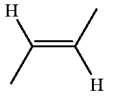 | 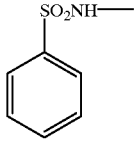 | 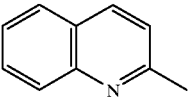 | 4 | FAB-MS: (m/z)656(M⁺)<br>¹H NMR(CDCl₃)<br>1.20–1.32(4H, m)2.64(2H, br s)3.18<br>(2H, br s)4.51(2H, s)5.58(1H, br s)<br>7.12–7.92(19H, m)8.24(2H, m) |
| 40 | 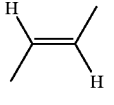 | 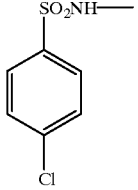 | | 3 | FAB-MS: (m/z)676(M⁺)<br>¹H NMR(CDCl₃)<br>1.25–1.33(2H, m)2.63–2.70(2H, m)3.10–<br>3.21(4H, m)3.50(2H, t J=7.92Hz)<br>4.34(2H, s)6.17(1H, br s)6.99–7.14<br>(3H, m)7.26(4H, m)7.39–7.78(13H, m)<br>7.87(1H, d J=7.92Hz)8.24(2H, m) |

TABLE 3-continued

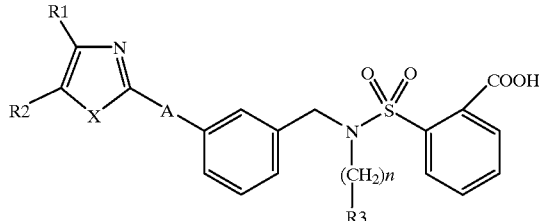

| Compound No. | 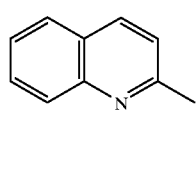 | A | R3 | n | Physicochemical properties |
|---|---|---|---|---|---|
| 41 | 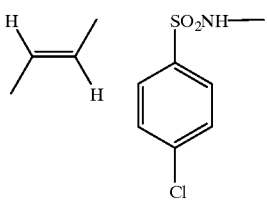 | H₃C-CH=CH- (cis) | 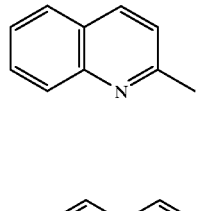 (4-Cl-C₆H₄-SO₂NH-) | 2 | FAB-MS: (m/z)663d(M⁺)608 476 244<br>¹H NMR(CDCl₃)<br>2.75(2H, s)3.30(2H, s)4.48(2H, s)5.98 (1H, br s)7.13(2H, m)7.43–7.93(14H, m)8.30(1H, d J=8.57Hz)8.35(1H, d J=8.91Hz) |
| 42 | 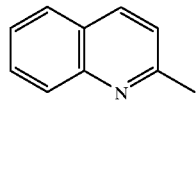 | H₃C-CH=CH- | 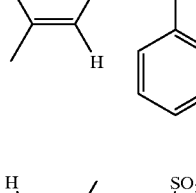 (4-Br-C₆H₄-SO₂NH-) | 2 | FAB-MS: (m/z)708(M⁺)522 244<br>¹H NMR(CDCl₃)<br>2.73(2H, s)3.30(2H, s)4.48(2H, s)7.12 (2H, s)7.39–7.91(16H, m)8.27(1H, d J=8.58Hz)8.33(1H, d J=8.91Hz) |
| 43 | 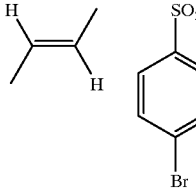 | H₃C-CH=CH- | 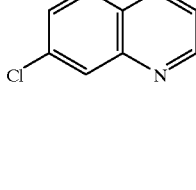 (4-F-C₆H₄-SO₂NH-) | 2 | FAB-MS: (m/z)646(M⁺)450 244<br>¹H NMR(CDCl₃)<br>2.75(2H, s)3.31(2H, s)4.48(2H, s)6.96 (2H, t)7.11(2H, d J=4.29Hz)7.42–7.92(14H, m)8.23(1H, d J=8.58Hz) 8.33(1H, d J=8.91Hz) |
| 44 | 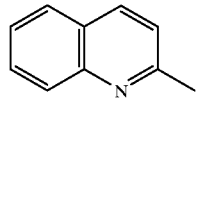 | H₃C-CH=CH- | C₆H₅-SO₂NH- | 2 | FAB-MS: (m/z)628(M⁺)483<br>¹H NMR(CDCl₃)<br>2.87(2H, dd J=12.2 5.94Hz)3.37(2H, m)4.00(3H, s)4.45(2H, s)7.22–7.75 (17H, m)7.80(1H, d J=7.92Hz)7.95(1H, dd J=6.1 1.5Hz)8.09Hz(1H, d J=8.25Hz) 8.16(1H, d J=8.9Hz) |
| 45 | 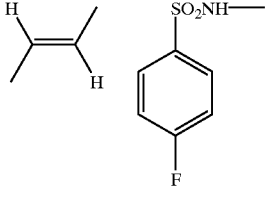 | H₃C-CH=CH- | 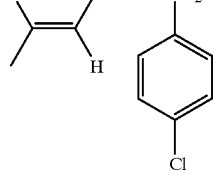 (4-Cl-C₆H₄-SO₂NH-) | 4 | FAB-MS: (m/z)724(M⁺)675<br>¹H NMR(CDCl₃)<br>1.21–1.40(4H, m)2.68–2.72(2H, m)3.22 (2H, br t J=6.93Hz)4.50(2H, s)5.59–5.64(1H, m)7.18(2H, d J=4.95Hz) 7.30–7.72(14H, m)7.89(1H, d J=7.59Hz) 8.13–8.17(2H, m) |

TABLE 3-continued

| Compound No. | R1, R2, X (ring) | A | R3 | n | Physicochemical properties |
|---|---|---|---|---|---|
| 46 | 7-chloro-2-methylquinoline | CH=C(CH3)(H) | 4-F-C6H4-SO2NH- | 4 | FAB-MS(m/z)708(M+)<br>1H NMR(CDCl3)<br>1.22–1.42(4H, m)2.68–2.72(2H, m)3.21(2H, br t)4.50(2H, s)5.54–5.60(1H, m)7.00–7.06(2H, m)7.15–7.17(2H, m)7.41(2H, dd J=1.98 8.58Hz)7.47–7.78(10H, m)7.88(1H, d J=7.26Hz)8.13–8.17(2H, m) |
| 47 | 7-chloro-2-methylquinoline | CH=C(CH3)(H) | 4-Br-C6H4-SO2NH- | 4 | FAB-MS: (m/z)68(M+)<br>1H NMR(CDCl3)<br>1.21–1.40(4H, m)2.67–2.75(2H, m)3.21(2H, br t J=6.60Hz)4.50(2H, s)5.58–5.63(1H, m)7.70(2H, d J=4.62Hz)7.38–7.66(12H, m)7.71(2H, d J=8.9Hz)7.88(1H, d J=7.26Hz)8.13–8.17(2H, m) |
| 48 | 7-chloro-2-methylquinoline | CH=C(CH3)(H) | 4-OCH3-C6H4-SO2NH- | 4 | FAB-MS: (m/z)720(M+)<br>1H NMR(CDCl3)<br>1.21–1.41(4H, m)2.67–2.74(2H, m)3.23(2H, br t J=6.93Hz)3.78(3H, s)4.50(2H, s)5.10–5.15(1H, m)6.86(2H, d J=8.91Hz)7.19–7.21(2H, m)7.44(2H dd J=1.81 8.75Hz)7.50–7.73(10H, m)7.91(1H, d J=7.92Hz)8.08–8.17(2H, m) |
| 49 | 7-chloro-2-methylquinoline | CH=C(CH3)(H) | 4-CH3-C6H4-SO2NH- | 4 | FAB-MS: (m/z)704(M+)<br>1H NMR(CDCl3)<br>1.20–1.41(4H, m)2.32(3H, s)2.67–2.70(2H, m)3.21(2H, br t J=6.93Hz)4.49(2H, s)5.22–5.29(1H, m)7.12–7.21(4H, m)7.41(2H, dd J=1.98 8.58Hz)7.47–7.72(10H, m)7.89(1H, d J=7.92Hz)8.07–8.16(2H, m) |
| 50 | 7-chloro-2-methylquinoline | CH=C(CH3)(H) | C6H5-SO2NH- | 4 | FAB-MS: (m/z)690(M+)<br>1H NMR(CDCl3)<br>1.20–1.40(4H, m)2.67–2.75(2H, m)3.21(2H, br t J=6.93Hz)4.50(2H, s)5.30–5.37(1H, m)7.06(1H, d J=6.27Hz)7.18(2H, d J=4.62Hz)7.36–7.75(14H, m)7.90(1H, d J=7.92Hz)8.13–8.16(2H, m) |

TABLE 3-continued

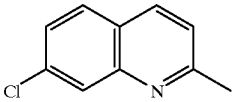

| Compound No. |  | A | R3 | n | Physicochemical properties |
|---|---|---|---|---|---|
| 51 | 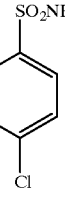 | 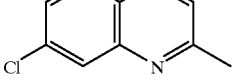 |  | 3 | FAB-MS: (m/z)710(M⁺)<br>¹H NMR(CDCl₃)<br>1.46–1.53(2H, m)2.51–2.60(2H, m)3.22 (2H, br t J=7.09Hz)4.48(2H, s)7.25 (1H, d J=7.26Hz)7.36–7.43(2H, m) 7.58–7.76(10H, m)7.82(1H, d J=16.2Hz) 7.93(2H, d J=8.58Hz)7.98–8.06(2H, m) 8.41(1H, d J=8.91Hz) |
| 52 | 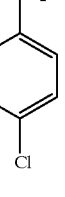 | 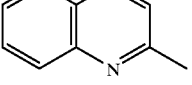 | 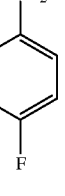 | 2 | FAB-MS: (m/z)696(M⁺)<br>¹H NMR(CDCl₃)<br>2.75–2.9(2H, m)3.30–3.35(2H, m)4.48 (2H, s)7.14(2H, d J=4.29Hz)7.25– 7.29(2H, m)7.42–7.64(10H, m)7.70–7.77 (2H, m)7.90(1H, d J=7.59Hz)8.22 (1H, d J=8.9Hz) |
| 53 | 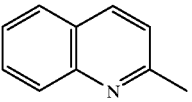 | —CH₂O— | 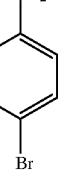 | 4 | FAB-MS: (m/z)6.78(M⁺)494 248<br>¹H NMR(CDCl₃)<br>1.10–1.28(4H, m)2.62–2.68(2H, m)3.07 (2H, br t J=6.60Hz)4.37(2H, s)5.36 (1H, br s)5.42(1H, s)6.78(1H, d J= 7.58Hz)6.91(1H, dd J=8.25Hz)7.00– 7.14(4H, m)7.45–7.76(8H, m)7.85(2H, t J=9.06Hz)8.22(2H, t J=7.43Hz) |
| 54 | 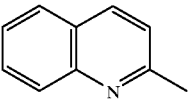 | —CH₂O— | 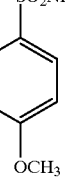 | 4 | FAB-MS: (m/z)737(M⁺)<br>¹H NMR(CDCl₃)<br>1.08–1.28(4H, m)2.58–2.66(2H, m)3.00– 3.10(2H, m)4.34(2H, s)5.33(2H, s) 6.77(1H, d J=7.25Hz)6.88(1H, dd J=8.25Hz)6.94(1H, s)7.10(1H, t)J= 7.75Hz)7.30–7.80(12H, m)8.12(1H, d J=8.92Hz)8.17(1H, d J=8.25Hz) |
| 55 |  | —CH₂O— |  | 4 | FAB-MS: (m/z)690(M⁺)<br>¹H NMR(CDCl₃)<br>1.08–1.18(2H, m)1.20–1.31(2H, m) 2.60–2.65(2H, m)3.03(2H t J=6.95Hz) 3.81(3H, s)4.36(2H, s)4.86 (1H, br s)5.46(2H, s)6.78(1H, d J= 7.58Hz)6.87–6.93(3H, m)7.02(1H, s) 7.12(1H, t J=7.75Hz)7.49–7.61 (3H, m)7.67–7.91(5H, m)7.84(1H, d J=7.91Hz)7.93(1H, d J=7.59Hz) 8.24–8.29(2H, m) |

TABLE 3-continued

[Structure: R1, R2 on thiazole/oxazole (X) ring connected to A, then phenyl-CH2-N(SO2-arylCOOH)-(CH2)n-R3]

| Compound No. | R2-[ring with R1, X, methyl] | A | R3 | n | Physicochemical properties |
|---|---|---|---|---|---|
| 56 | 2-methylquinoline | —CH₂O— | 4-methylphenyl-SO₂NH— | 4 | FAB-MS: (m/z)674(M⁺)<br>¹H NMR(CDCl₃)<br>1.07–1.16(2H, m)1.18–1.29(2H, m)2.36(3H, s)2.59–2.65(3H, m)3.04(2H, t J=6.77Hz)4.35(3H, s)4.95–5.02(1H, m)5.44(2H, s)6.78(1H, d J=7.58Hz)6.91(1H, dd J=7.92Hz)7.01(1H, s)7.11(1H, t J=7.76Hz)7.19(2H, d J=7.92Hz)7.47–7.78(8H, m)7.83(1H, d J=7.91Hz)7.91(1H, d J=7.59Hz)8.24(2H, d J=8.58Hz) |
| 57 | 2-methylquinoline | —CH₂O— | phenyl-SO₂NH— | 4 | FAB-MS: (m/z)660(M⁺)<br>¹H NMR(CDCl₃)<br>1.05–1.15(2H, m)1.17–1.29(2H, m)2.60–2.67(2H, m)3.02(2H, t J=6.93Hz)4.35(2H, s)4.94–4.98(1H, m)5.50(2H, s)6.78(1H, d J=7.58Hz)6.93(1H, dd J=7.58Hz)7.05(1H, s)7.12(1H, t J=7.92Hz)7.40–7.62(6H, m)7.69–7.80(5H, m)7.85(1H, d J=7.92Hz)7.95(1H, d J=7.92Hz)8.27–8.32(2H, m) |
| 58 | 2-methylquinoline | —CH₂O— | 4-chlorophenyl-SO₂NH— | 3 | FAB-MS: (m/z)674(M⁺)539<br>¹H NMR(CDCl₃)<br>1.25–1.37(2H, m)2.58–2.67(2H, m)3.14(2H, t J=6.43Hz)4.34(2H, s)5.52(2H, s)6.55–6.63(1H, m)6.77(1H, d J=7.58Hz)6.93(1H, d J=7.91Hz)7.01(1H, m)7.12(1H, t J=7.92Hz)7.32(2H, d J=8.58Hz)7.51–7.67(6H, m)7.71–7.90(4H, m)8.30(2H, d J=8.57Hz) |
| 59 | 2-methylquinoline | —CH₂O— | 4-chlorophenyl-SO₂NH— | 2 | FAB-MS: (m/z)666(M⁺)<br>¹H NMR(CDCl₃)<br>2.66(2H, br s)3.21(2H, br s)4.32(2H, br s)5.54(2H, br s)6.75(1H, d J=6.93Hz)6.91(1H, d J=8.58Hz)7.00(21H, s)7.10(1H, t J=7.75Hz)7.24–7.27(2H, m)7.47–7.61(6H, m)7.75–7.93(4H, m)8.26–8.43(2H, m) |
| 60 | 2-methylquinoline | —CH₂O— | 4-fluorophenyl-SO₂NH— | 2 | FAB-MS: (m/z)650(M⁺)<br>¹H NMR(CDCl₃)<br>2.65–2.70(2H, m)3.23(2H, br t)4.33(2H, s)5.50(2H, s)6.76(1H, d J=7.59Hz)6.89–7.00(4H, m)7.10(1H, t J=7.75Hz)7.42–7.62(6H, m)7.73–7.92(4H, m)8.23–8.32(2H, m) |

TABLE 3-continued

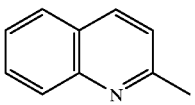

| Compound No. | 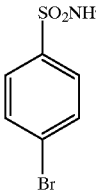 | A | R3 | n | Physicochemical properties |
|---|---|---|---|---|---|
| 61 | 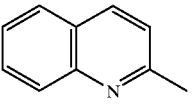 | —CH₂O— | 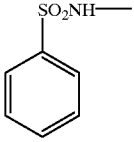 | 2 | FAB-MS: (m/z)710(M⁺)<br>¹H NMR(CDCl₃)<br>2.64–2.70(2H, m)3.21(2H, t, J=5.61Hz)<br>4.32(2H, s)5.57(2H, s)6.75(1H, d J=7.26Hz)6.92(1H, dd J=2.31 8.24Hz)<br>7.01(1H, s)7.11(1H, t J=7.92Hz)7.46<br>(4H, m)7.49–7.65(4H, m)7.77–7.95<br>(4H, m)8.28–8.36(2H, m) |
| 62 | 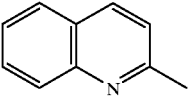 | —CH₂O— | 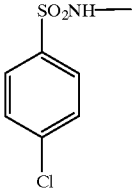 | 2 | FAB-MS: (m/z)633(M⁺)<br>¹H NMR(CDCl₃)<br>2.65–2.70(2H, m)3.18(2H, br t J=5.61Hz)<br>4.29(2H, s 5.59(2H, s)6.73(1H,<br>d J=7.59Hz)6.96(1H, dd J=1.98 8.25Hz)<br>7.00(1H, s)7.09(1H, t J=7.92Hz)<br>7.34(2H, t J=7.43Hz)7.42–7.71(7H,<br>m)7.76–7.84(2H, m)7.88(1H, d J=7.92Hz)<br>7.98(1H, d J=7.59Hz)8.33(1H, d<br>J=8.91Hz)8.34(1H, d J=8.25Hz) |
| 63 | 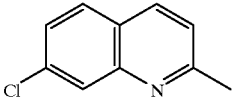 | —CH₂O— | 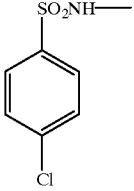 | 5 | FAB-MS: (m/z)721(M⁺)<br>¹H NMR(CDCl₃)<br>0.89–0.99(2H, m)1.11–1.27(4H, m)2.67–<br>2.74(2H, m)3.04(2H, t J=6.93Hz)<br>4.38(2H, s)5.42(2H, s)6.79(1H, d J=<br>7.26Hz)6.91(1H, dd J=1.65 8.25Hz)<br>7.02(1H, s)7.13(1H, t J=7.92Hz)7.36<br>(2H, d J=8.58Hz)7.47–7.78(8H, m)<br>7.84(1H, d J=8.24Hz)7.91(1H, d J=7.59Hz)<br>8.24(2H, d J=8.58Hz) |
| 64 | 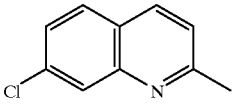 | —CH₂O— | 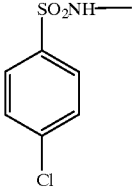 | 2 | FAB-MS: (m/z)700(M⁺)<br>¹H NMR(CDCl₃)<br>2.70–2.79(2H, m)3.26(2H, t J=5.78Hz)<br>4.34(2H, s)5.47(2H, s)5.99–6.08(1H,<br>m)6.78(1H, d J=7.58Hz)6.91(1H,<br>dd J=1.98 8.25Hz)6.98(1H, s)7.12(1H,<br>t J=7.92Hz)7.28(2H, d J=8.58Hz)<br>7.50–7.81(8H, m)7.93(1H, d J=7.26Hz)<br>8.21(1H, d J=1.98Hz)8.27(1H, d<br>J=8.58Hz) |
| 65 | | —CH₂O— | | 4 | FAB-MS: (m/z)730(M⁺)<br>¹H NMR(CDCl₃)<br>1.18–1.36(4H, m)2.68–2.74(2H, m)3.13<br>(2H, t J=6.76Hz)4.39(2H, s)6.80(1H,<br>d J=7.59Hz)6.90(1H, dd J=7.92Hz)<br>6.97(1H, m)7.14(1H, J=7.92Hz)7.35<br>(2H, d J=8.58Hz)7.48–7.70(7H, m)<br>7.76(1H, d J=8.58Hz)7.88(1H, d J=7.26Hz)<br>8.14(1H, d J=1.65Hz)8.20(1H,<br>d J=8.58Hz) |

TABLE 3-continued

| Compound No. | R2—[thiazole]—R1 (2-methyl) | A | R3 | n | Physicochemical properties |
|---|---|---|---|---|---|
| 66 | 2-methylquinolin-yl | —CH$_2$CH$_2$— | 4-Cl-C$_6$H$_4$-SO$_2$NH— | 4 | FAB-MS: (m/z)692(M$^+$)600 508 246<br>$^1$H NMR(CDCl$_3$)<br>1.10–1.30(4H, m)3.60–2.68(2H, m)3.05–3.13(4H, m)3.44(2H, t J=7.92Hz)<br>4.38(2H, s)5.74–5.81(1H, m)7.01–7.11(3H, m)7.26–7.37(4H, m)7.46(1H, t d J=1.32–7.5Hz)7.53–7.68(5H, m)7.72–7.88(3H, m)8.22(1H, d J=8.25Hz)<br>8.34(1H, d J=8.58Hz) |
| 67 | 2-methylquinolin-yl | —CH$_2$CH$_2$— | 4-F-C$_6$H$_4$-SO$_2$NH— | 4 | FAB-MS: (m/z)676(M$^+$)492 246<br>$^1$H NMR(CDCl$_3$)<br>1.14–1.30(4H, m)2.59–2.67(2H, m)3.08–3.13(4H, m)3.44(2H, t J=7.92Hz)<br>4.38(2H, s)5.60–5.70(1H, m)6.99–7.13(5H, m)7.26(1H, s)7.35(1H, d J=8.58Hz)<br>7.43–7.64(4H, m)7.71–7.88(5H, m)<br>8.21(1H, d J=8.58Hz)8.34(1H, d J=8.58Hz) |
| 68 | 2-methylquinolin-yl | —CH$_2$CH$_2$— | 4-CH$_3$-C$_6$H$_4$-SO$_2$NH— | 4 | MS: (m/z)672(M$^+$)488 246<br>$^1$H NMR(CDCl$_3$)<br>1.10–1.30(4H, m)2.34(3H, s)2.59–2.65(2H, m)3.04–3.12(4H, m)3.42(2H, t J=7.75Hz)4.37(2H, s)5.25–5.32(1H, m)<br>7.00–7.12(3H, s)7.17(2H, d J=7.92Hz)<br>7.25(1H, d J=7.59Hz)7.32(1H, d J=8.58Hz)7.42–7.64(6H, m)7.71–7.81(2H, m)7.87(1H, d J=7.26Hz)8.18 1H, d J=8.58Hz)8.34(1H, d J=8.25Hz) |
| 69 | 2-methylquinolin-yl | —CH$_2$CH$_2$— | 4-OCH$_3$-C$_6$H$_4$-SO$_2$NH— | 4 | FAB-MS: (m/z)688(M$^+$)596 504 246<br>$^1$H NMR(CDCl$_3$)<br>1.09–1.33(4H, m)2.59–2.68(2H, m)3.04–3.12(4H, m)3.42(2H, t J=7.75Hz)<br>3.79(3H, s)4.37(2H, s)6.85(2H, d J=8.91Hz)7.00–7.12(3H, m)7.25(1H, d J=6.27Hz)7.32(1H, d J=8.58Hz)7.42–7.58(3H, m)7.62–7.81(5H, m)7.88(1H, d J=7.26Hz)8.18(1H, d J=8.58Hz)<br>8.24(1H, d J=8.58Hz) |
| 70 | 2-methylquinolin-yl | —CH$_2$CH$_2$— | 4-Br-C$_6$H$_4$-SO$_2$NH— | 4 | FAB-MS: (m/z)736(M$^+$)552 246<br>$^1$H NMR(CDCl$_3$)<br>1.11–1.29(4H, m)2.58–2.64(2H, m)3.07–3.12(4H, m)3.43(2H, t J=7.75Hz)<br>4.37(2H, s)5.78–5.82(1H, m)7.01–7.13(3H, m)7.25(1H, d J=2.97Hz)7.34(1H, d J=8.54Hz)7.42–7.47(3H, m)7.52–7.62(5H, m)7.71–7.87(3H, m)8.21(1H, d J=8.58Hz)8.33(1H, d J=8.58Hz) |

TABLE 3-continued

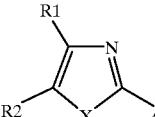

| Compound No. | 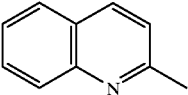 | A | R3 | n | Physicochemical properties |
|---|---|---|---|---|---|
| 71 | 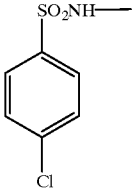 | —CH$_2$CH$_2$— | 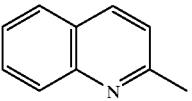 | 2 | FAB-MS: (m/z)664(M$^+$)480 246<br>$^1$H NMR(CDCl$_3$)<br>2.57–2.69(2H, m)2.99–3.07(2H, m)3.10–3.18(2H, m)3.18–3.27(2H, m)4.41(2H, m)7.00–7.04(1H, m)7.09(1H, br s)7.18–7.21(2H, m)7.41(1H, d J=8.25Hz)7.52–7.79(9H, m)7.85–8.00(3H, m)8.25(1H, d J=8.58Hz) |
| 72 | 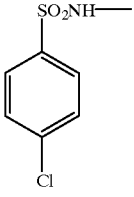 | —CH$_2$CH$_2$— | 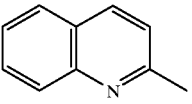 | 3 | FAB-MS: (m/z)678(M$^+$)<br>$^1$H NMR(CDCl$_3$)<br>1.25–1.33(2H, m)2.63–2.70(2H, m)3.10–3.21(4H, m)3.50(2H, t J=7.92Hz)4.34(2H, s)6.17–6.24(1H, m)6.99–7.14(3H, m)7.26–7.33(3H, m)7.40(1H, d J=8.58Hz)7.48(1H, t d J=7.59 1.54Hz)7.56–7.67(5H, m)7.79–7.88(3H, m)8.27(1H, d J=8.58Hz)8.42(1H, d J=8.58Hz) |
| 73 | 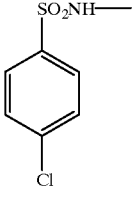 | —CH$_2$CH$_2$— | 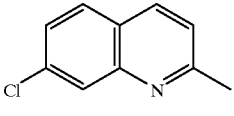 | 5 | FAB-MS: (m/z)706(M$^+$)672<br>$^1$H NMR(CDCl$_3$)<br>0.89–1.01(2H, m)1.09–1.25(4H, m)2.64–2.72(2H, m)3.02–3.14(4H, m)3.47(2H, t J=7.75Hz)4.38(2H, s)5.63–5.70(1H, m)7.00–7.13(3H, m)7.26–7.29(1H, m)7.36(2H, d J=7.26Hz)7.44–7.83(9H, m)7.91(1H, d J=7.26Hz)8.23(1H, d J=8.58Hz)8.41(1H, d J=8.58Hz) |
| 74 | 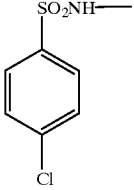 | —CH$_2$CH$_2$— | 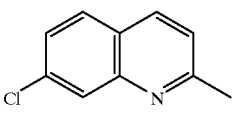 | 4 | FAB-MS: (m/z)726(M$^+$)542 383 280<br>$^1$H NMR(CDCl$_3$)<br>1.18–1.35(4H, m)2.69(2H, br d J=4.62Hz)3.05–3.13(4H, m)3.35(2H, t J=7.76Hz)4.37(1H, s)5.42–5.50(1H, m)7.01–7.15(3H, m)7.20(1H, m)7.28–7.36(3H, m)7.44–7.74(7H, m)7.87(1H, d J=7.59Hz)8.11(1H, d J=8.58Hz)8.21(1H, d J=1.32Hz) |
| 75 | 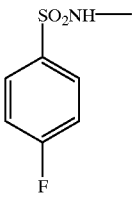 | —CH$_2$CH$_2$— | | 4 | FAB-MS: (m/z)710(M$^+$)526 228<br>$^1$H NMR(CDCl$_3$)<br>1.19–1.37(4H, m)2.70(2H, br d J=4.95Hz)3.05–3.15(4H, m)3.36(2H, br t J=7.76Hz)4.38(2H, s)5.35–5.42(1H, m)7.02–7.15(5H, m)7.21(1H, s)7.23 1H, d J=8.25Hz)7.44–7.78(7H, m)7.87(1H, d J=7.59Hz)8.12(1H, d J=8.25Hz)8.21(1H, s) |

TABLE 3-continued

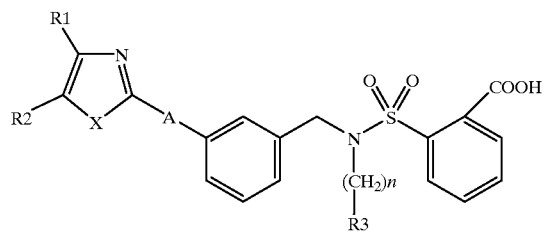

| Compound No. | R1, R2, X (2-methyl) | A | R3 | n | Physicochemical properties |
|---|---|---|---|---|---|
| 76 | 7-Cl quinoline | —CH$_2$CH$_2$— | SO$_2$NH—C$_6$H$_4$—CH$_3$ | 4 | FAB-MS: (m/z)706(M$^+$)614 522 349<br>$^1$H NMR(CDCl$_3$)<br>1.15–1.38(4H, m)2.37(3H, s)2.67–2.73<br>(2H, m)3.05–3.13(4H, m)3.34(2H, t<br>7.92Hz)4.37(2H, s)5.05–5.13(1H, m)<br>7.01–7.14(3H, m)7.20–7.30(4H, m)7.44–<br>7.69(6H, m)7.72(1H, d J=8.58Hz)<br>7.90(1H, d J=7.92Hz)8.05(1H, d J=8.25Hz)<br>8.20(1H, d J=1.98Hz |
| 77 | 7-Cl quinoline | —CH$_2$CH$_2$— | SO$_2$NH—C$_6$H$_4$—OCH$_3$ | 4 | FAB-MS: (m/z)722(M$^+$)688 538<br>$^1$H NMR(CDCl$_3$)<br>1.15–1.39(4H, m)2.63–2.71(2H, m)3.04–<br>3.13(4H, m)3.34(2H, t J=7.92Hz)<br>3.80(3H, s)4.37(2H, s)6.88(2H, d J=<br>8.91Hz)7.01–7.14(3H, m)7.19(1H, s)<br>7.28(1H, d J=8.58Hz)7.43–7.73(7H, m)<br>7.88(1H, d J=7.59Hz)8.09(1H, d J=<br>8.58Hz)8.21(1H, d J=1.65Hz) |
| 78 | 7-Cl quinoline | —CH$_2$CH$_2$— | SO$_2$NH—C$_6$H$_4$—Br | 4 | FAB-MS: (m/z)770(M$^+$)<br>$^1$H NMR(CDCl$_3$)<br>1.12–1.32(4H, m)2.65–2.72(2H, m)3.05–<br>3.15(4H, m)3.35(2H, t J=7.92Hz)<br>4.38(2H, s)7.02–7.15(3H, m)7.20(1H,<br>s)7.30(1H, d J=8.58Hz)7.45–7.53(4H,<br>m)7.56–7.66(4H, m)7.73(1H, d J=<br>8.58Hz)7.56–7.66(4H, m)7.73(1H, d<br>J=8.58Hz)7.86(1H, d J=7.26Hz)8.12<br>(1H, d J=8.25Hz)8.21(1H, d J=1.98Hz |
| 79 | 7-Cl quinoline | —CH$_2$CH$_2$— | SO$_2$NH—C$_6$H$_4$—Cl | 2 | FAB-MS: (m/z)699(M$^+$)<br>$^1$H NMR(CDCl$_3$)<br>2.70–2.77(2H, m)3.10(2H, t J=7.75Hz)<br>3.23–3.28(2H, m)3.43(2H, t J=7.91Hz)<br>4.35(2H, s)6.99–7.13(3H, m)7.26–<br>7.29(3H, m)7.36(1H, d J=8.58Hz)7.48–<br>7.54(4H, m)7.57–7.64(2H, m)7.76<br>(1H, d J=8.91Hz)7.91(1H, d J=7.92Hz)<br>8.18(1H, d J=8.58Hz)8.26(1H, d J=1.65Hz) |
| 80 | 7-Cl quinoline | —CH$_2$CH$_2$— | SO$_2$NH—C$_6$H$_4$—Cl | 3 | FAB-MS: (m/z)712(M$^+$)528<br>$^1$H NMR(CDCl$_3$)<br>1.28–1.38(2H, m)2.68–2.75(2H, m)3.09<br>(2H, t J=7.76Hz)3.20–3.25(2H, m)<br>3.39(2H, t J=7.92Hz)4.35(2H, s)5.86<br>(1H, br t)7.00–7.15(3H, m)7.25–7.26<br>(2H, m)7.33(2H, d J=8.58Hz)7.48–<br>7.56(2H, m)7.59–7.68(4H, m)7.76(1H,<br>d J=8.91Hz)7.86(1H, d J=7.92Hz)8.17<br>(1H, d J=8.58Hz)8.27(1H, d |

TABLE 3-continued

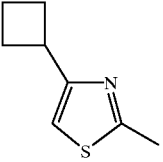

| Compound No. | 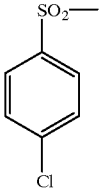 | A | R3 | n | Physicochemical properties |
|---|---|---|---|---|---|
| 81 | 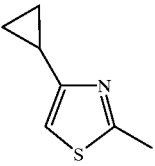 | —CH$_2$O— | 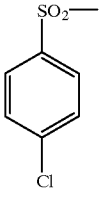 | 5 | FAB-MS: (m/z)703(M$^+$)669 519<br>$^1$H NMR(CDCl$_3$)<br>1.11–1.19(2H, m)1.25–1.36(2H, m)1.47–1.58(2H, m)1.85–2.13(2H, m)2.17–2.31(2H, m)2.34–2.45(2H, m)2.87–2.96(2H, m)3.10(2H, t J=7.26Hz)3.74(1H, quint J=8.49Hz)4.39(2H, s)5.38(2H, s)6.80–6.88(2H, m)6.94–6.96(2H, m)7.13(1H, t J=7.92Hz)7.50–7.70(5H, m)7.79(2H, d J=8.58Hz)7.96(1H, d J=7.59Hz) |
| 82 | 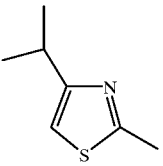 | —CH$_2$O— | 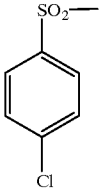 | 5 | FAB-MS: (m/z)689(M$^+$)655 505 244<br>$^1$H NMR(CDCl$_3$)<br>0.83–0.91(2H, m)0.91–1.00(2H, m)1.14–1.22(2H, m)1.26–1.38(2H, m)1.51–1.62(2H, m)2.707–2.17(1H, m)2.91–2.97(2H, m)3.12(2H, t J=7.26Hz)4.39(2H, s)5.30(2H, s)6.81–6.88(3H, m)6.93(1H, br s)7.15(1H, t J=7.92Hz)7.52(2H, d J=8.57Hz)7.56–7.71(3H, m)7.81(2H, d J=8.58Hz)7.95(1H, d J=7.59Hz) |
| 83 | 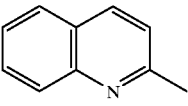 | —CH$_2$O— | 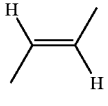 | 5 | FAB-MS: (m/z)691(M$^+$)657 507 473<br>$^1$H NMR(CDCl$_3$)<br>1.11–1.19(2H, m)1.26–1.33(8H, m)1.47–1.59(2H, m)2.88–2.94(2H, m)3.08–3.13(2H, m)3.19(1H, quint J=6.93Hz)4.39(2H, s)5.38(2H, s)6.81–6.88(2H, s)6.93(1H, s)6.95(1H, br s)7.13(1H, t J=7.92Hz)7.52(2H, d J=8.58Hz)7.56–7.70(3H, m)7.79(2H, d J=8.58Hz)7.96(1H, d J=7.59Hz) |
| 84 | 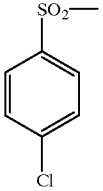 | 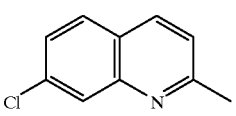 | SO$_2$— 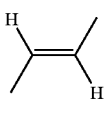 | 5 | FAB-MS: (m/z)689(M$^+$)244<br>$^1$H NMR(CDCl$_3$)<br>1.18–1.11(2H, m)1.22–1.39(2H, m)1.42–1.50(2H, m)2.8–2.84(2H, m)3.20(2H, br t J=7.78Hz)4.50(2H, s)7.14–7.16(2H, s)7.42–7.82(15H, m)7.91(1H, d J=7.26Hz)8.22–8.27(2H, m) |
| 85 | 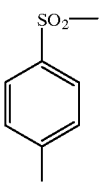 | | | 5 | FAB-MS: (m/z)723(M$^+$)<br>$^1$H NMR(CDCl$_3$)<br>1.17–1.23(2H, m)1.24–1.37(2H, m)1.42–1.55(2H, m)2.82–2.87(2H, m)3.21(2H, br t J=6.93Hz)4.50(2H, s)7.17–7.22(2H, m)7.42–7.88(14H, m)7.91(1H, d J=7.59Hz)8.13–8.16(2H, m) |

TABLE 3-continued

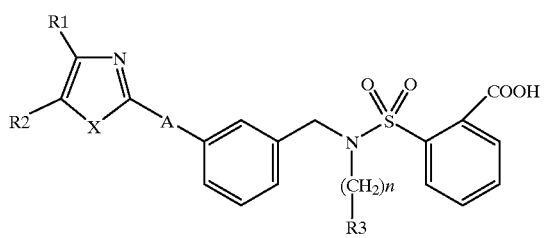

| Compound No. |  A | R3 | n | Physicochemical properties |
|---|---|---|---|---|
| 86 | 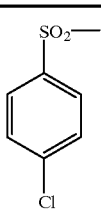 —CH₂CH₂— | 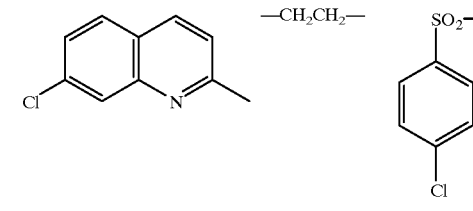 SO₂— | 5 | FAB-MS: (m/z)691(M⁺)507<br>¹H NMR(CDCl₃)<br>1.05–1.15(2H, m)1.21–1.32(2H, m)1.41–1.51(2H, m)2.81–2.88(2H, m)3.01–3.18(4H, m)3.37–3.45(2H, m)4.37(2H, s)6.97–7.07(3H, m)7.26–7.31(2H, m)7.47–7.61(5H, m)7.67–7.82(5H, m)7.92(1H, d J=7.26Hz)8.16(1H, d J=8.25Hz)8.36(1H, d J=8.25Hz) |
| 87 |  —CH₂CH₂— | 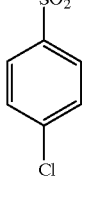 SO₂— | 5 | FAB-MS: (m/z)725(M⁺)<br>¹H NMR(CDCl₃)<br>1.08–1.18(2H, m)1.22–1.23(2H, m)1.45–1.56(2H, m)2.85–2.91(2H, m)3.04–3.12(4H, m)3.38(2H, t J=7.76Hz)4.38(2H, s)6.99–7.15(3H, m)7.20–7.28(2H, m)7.44–7.68(5H, m)7.68–7.83(4H, m)7.92(1H, d J=6.93Hz)8.08(1H, d J=8.58Hz)8.24(1H, d J=1.65Hz) |
| 88 | 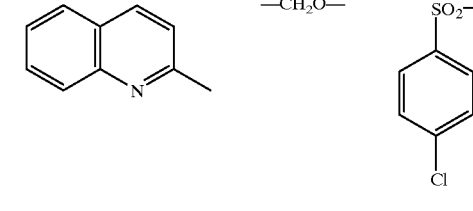 —CH₂O— | 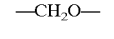 SO₂— | 5 | FAB-MS: (m/z)693(M⁺)<br>¹H NMR(CDCl₃)<br>0.95–1.06(2H, m)1.16–1.27(2H, m)1.37–1.49(2H, m)2.81–2.86(2H, m)3.01(2H, t J=7.43Hz)4.35(2H, s)5.46(2H, s)6.77(1H, d J=7.58Hz)6.90(1H, dd J=1.82 8.08Hz)7.03(1H, s)7.11(1H, t J=7.76Hz)7.47–7.64(5H, m)7.69–7.80(5H, m)7.85(1H, d J=7.91Hz)7.96(1H, dd J=1.49 7.765Hz)8.25–8.31(2H, m) |
| 89 | 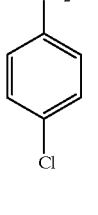 —CH₂O— | 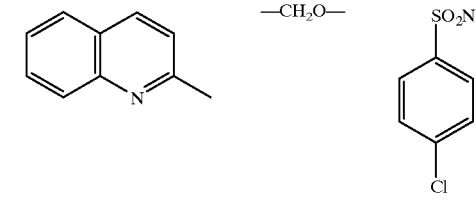 SO₂NH— | 4 | FAB-MS: (m/z)694(M⁺)510 248<br>¹H NMR(CDCl₃)<br>1.10–1.27(4H, m)2.61–2.68(2H, m)3.07(2H, br t J=6.93Hz)4.37(2H, s)5.44(2H, s)6.78(1H, d J=7.25Hz)6.91(1H, d J=8.24Hz)7.00(1H, s)7.09–7.15(1H, m)7.32(2H, d J=8.91Hz)7.46–7.78(8H, m)7.82–7.89(2H, m)8.21–8.26(2H, m) |
| 90 | 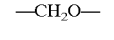 | 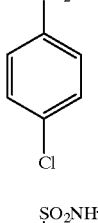 | 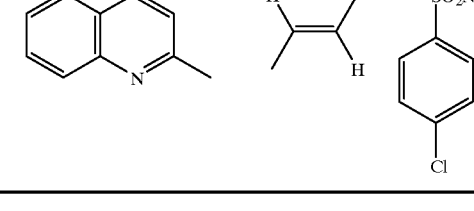 SO₂NH— | 4 | FAB-MS: (m/z)690(M⁺)506 244<br>¹H NMR(CDCl₃)<br>1.20–1.39(4H, m)2.60–2.67(2H, m)3.15–3.21(2H, m)4.51(2H, s)5.98–6.02(1H, br s)7.03–7.17(2H, m)7.25–7.31(2H, m)7.36(1H, d J=7.26Hz)7.43–7.79(12H, m)7.86(1H, d J=7.59Hz)8.23–8.30(2H, m) |

Example 12

Preparation of ethyl 2-{N-[4-(4-chlorobenzenesulfonylamino)butyl]-N-{3-[(4-isopropyl-2-thiazoyl)methoxy]benzyl}}sulfamoylbenzoate (Compound No.1c)

2.15 g (3.11 mmol) of 2-{N-[4-(4-chlorobenzenesulfonylamino)butyl]-N-{3-[(4-isopropyl-2-thiazolyl)methoxy]benzyl}}sulfamoylbenzoic acid (Compound No.1) was mixed with 16 ml of 1,2-dichloroethane and 0.41 ml (4.7 mmol) of oxalyl chloride and stirred in the presence of a catalytic amount of N,N-dimethylmamide at room temperature. The reaction solution was evaporated in vacuo for removal of the solvent and stirred together with 12 ml of ethanol, 12 ml of 1,2-dichloroethane and 0.65 ml (4.66 mmol) of triethylamine at room temperature for 1 hour. The reaction solution was mixed with water and saturated aqueous sodium hydrogen carbonate for neutralization and then extracted with chloroform. The chloroform layer was washed with saturated aqueous sodium chloride, dried over anhydrous magnesium sulfate and evaporated in vacuo for removal of the solvent. The residue was purified by silica gel column chromatography (eluent; n-hexane:ethyl acetate=3:1) to give 1.42 g of the title compound in a yield of 63.5%.

$^1$H-NMR(CDCl$_3$): 1.23–1.41(13H,m) 2.82(2H,m) 3.06–3.17(3H,m) 4.38–4.45(4H,m) 4.83(1H,t) 5.26(2H,s) 6.90(4H,d J=0.66 Hz) 7.22(1H,m) 7.45(2H,d J=1.98 6.6 Hz) 7.51–7.65(3H,m) 7.74(2H,d J=1.98 6.6 Hz) 7.83(1H,m).

Similarly, the compounds of Examples 13 and 14 were prepared.

Example 13

Preparation of ethyl 2-{N-[4-(4-methylbenzenesulfonylamino)butyl]-N-{3-[(4-cyclobutyl-2-thiazolyl)methoxy]benzyl}}sulfamoylbenzoate (Compound No.5c)

$^1$H-NMR(CDCl$_3$): 1.22–1.41(7H,m) 1.84–2.39(6H,m) 2.41(3H,s) 2.80(2H,m) 3.16(2H,m) 3.67(1H,quint) 4.37–4.45(4H,m) 4.61(1H,t J=6.27 Hz) 5.27(2H,s) 6.88–6.92(4H,m) 7.22–7.29(3H,m) 7.50–7.62(3H,m) 7.68 (2H,d J=8.24 Hz) 7.82(1h,d J=7.25 Hz).

Example 14

Preparation of ethyl 2-{N-[4-(4-chlorobenzenesulfonylamino)butyl]-N-{3-[4-cyclobutyl-2-thiazolyl)ethyl]benzyl}}sulfamoylbenzoate (Compound No.29c)

$^1$H-NMR(CDCl$_3$): 1.21.41(7H,m) 1.87–2.39(6H,m) 2.80 (2H,m) 3.14(2H,br s) 3.22(2H,m) 4.40(4H,m) 5.04(1H,t J=5.94 Hz) 6.75(1H,s) 7.08(3H,m) 7.20(1H,m) 7.45(2H,dd J=6.6 1.98 Hz) 7.51–7.65(3H,m) 7.73(2H,d J=8.25 Hz) 7.82(1H,d J=8.24 Hz).

Example 15

Preparation of 5-{2-{N-[4-(4-chlorobenzenesulfonylamino)butyl]-N-{3-[(4-isopropyl-2-thiazolyl)methoxylbenzyl}}sulfamoylphenyl}-1H-tetrazole (Compound No.91)

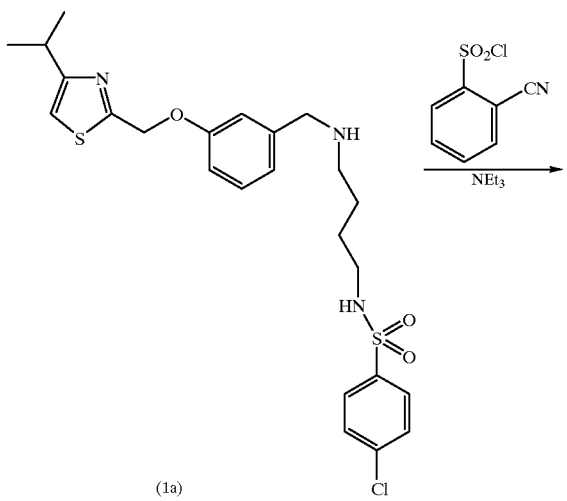

(1a)

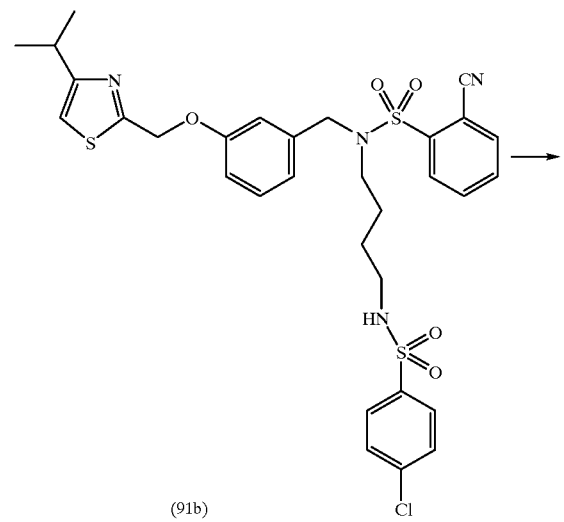

(91b)

129
-continued

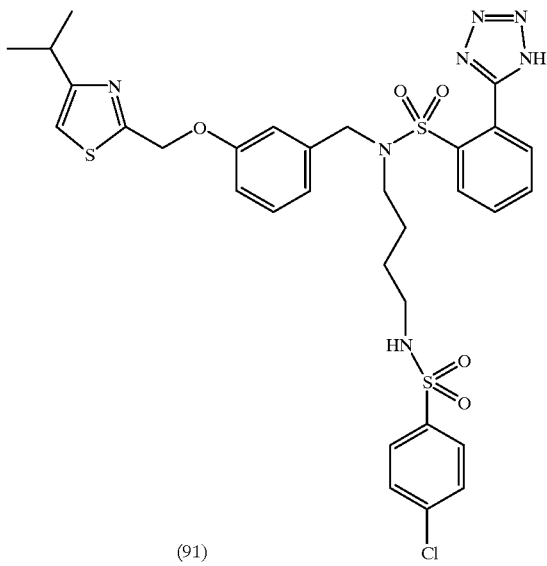

(91)

3.5 g (6.4 mmol) of the hydrochloride of the product in Example 9 (Compound 1a) was dissolved in 75 ml of 1,2-dichloroethane and stirred together with 2.7 ml of triethylamine and 1.7 g (1.3 eq) of 2-chlorosulfonylbenzonitrile at room temperature overnight. The organic layer was washed with water and saturated aqueous sodium chloride, dried over anhydrous magnesium sulfate and evaporated in vacuo for removal of the solvent. The residue was purified by silica gel column chromatography (eluent; chloroform to chloroform:methanol=99:1) to give 3.9 g of 2-{N-[4-(4-chlorobenzenesulfonylamino)butyl]-N-{3-[(4-isopropyl-2-thiazolyl)methoxylbenzyl]}sulfamoylbenzonitrile (Compound No.91b) in a yield of 89%.

FAB=MS(m/z): 673(M+); $^1$H-NMR(CDCl$_3$): 1.32(6H,d, J=6.93 Hz),1.42(4H,m),2.85(2H, m),3.11(1H,m),3.29(2H, m),4.42(2H,m),4.62(1H,m),5.29(2H,s), 6.84–6.89(3H,m), 6.91(1H,s),7.22(1H,m),7.47(2H,dd,J=8.58,1.82 Hz), 7.65–7.78(4H,m),7.88(1H,dd,J=1.98,7.26 Hz),8.07(1H, m).

3.8 g (5.6 mmol) of the above-mentioned product (Compound No.91b) was dissolved in 100 ml of toluene and stirred together with 3.7 ml (5.0 eq) of trimethylsilyl azide and 702 mg (0.5 eq) of dibutyltin oxide under heating at 70° C. for 28 hours. The solvent was distilled off in vacuo, and 50 ml of 1N sodium hydroxide and 50 ml of water were added to the residue. The insolubles were filtered out, and the filtrate was washed with 100 ml of ether. The aqueous layer was acidified with 6N hydrochloric acid and extracted with chloroform. The solvent was distilled off in vacuo, and the residue was purified by silica gel column chromatography (eluent; chloroform to chloroform:methanol= 99:1–95:5) to give 3.1 g of an oily substance in a yield of 78%. The oily substance was dissolved in 8.4 ml of 1N sodium hydroxide and 50 ml of water and acidified (pH 3.0) with iN hydrochloric acid, and the deposited precipitate was filtered off to give 2.4 g of the title compound (Compound No.91).

FAB-MS(m/z): 716(M+); $^1$H-NMR(CDCl$_3$): 1.16(4H,m), 1.27(6H,d,J=6.93 Hz),2.73(2H, m),2.87(2H,m),3.07(1H,m), 4.08(2H,s),5.30(2H,m),6.74–6.91 (4H,m),7.20(1H,t,J=7.76 Hz),7.46(2H,m),7.68–7.80(4H,m),7.9 7(1H,dd,J=1.65,7.32 Hz),8.08(1H,dd,J=1,65,5.66 Hz).

130

Test Examples

Next, the excellent antagonistic effects on the receptors for both mediators LTD$_4$ and TXA$_2$ and anti-allergic effects of the 2-sulfamoylbenzoic acid derivatives of the present invention will be demonstrated by referring to Test Examples.

Compounds of the present invention were tested on the LTD$_4$ inhibitory effects, TXA$_2$ inhibitory effects and anti-asthmatic effects. The test procedures and the test results were as follows.

Test Example 1
(LTD$_4$ antagonistic effects)

Guinea pigs were bled to death, and the ilea were excised and made into ileum preparations. The ileum preparations were suspended with a 1 g load in Magnus tubes filled with 2 ml Tyrode solution maintained at 37° C. under aeration with a 95% O$_2$-5% CO$_2$ gas mixture, and LTD$_4$-induced constrictions were isotonically recorded.

After equilibration of the tonuses of the ilea, constrictive responses to cumulative addition of 0.05–3.5 ng/ml LTD$_4$ were observed. After the constrictive responses reached equilibrium, LTD$_4$ was added again cumulatively 5 minutes after pre-treatment with a test substance to induce constriction. The pA$_2$ values were calculated in accordance with Van Rossum's method. The results are shown below in Table 4.

Test Example 2
(TXA$_2$ antagonistic effects)

Guinea pigs were bled to death, and the tracheae were excised and made into tracheal muscle strips in accordance with Takagi et al. The strips were suspended with a 1 g load in Magnus tubes filled with 2 ml Tyrode solution maintained at 37° C. under aeration with a 95% O$_2$-5% CO$_2$ gas mixture, and U-46619-induced constrictions were isotonically recorded.

After equilibration of the tonuses of the strips, constrictive responses to cumulative addition of $10^{-10}$–$10^{-7}$M U-46619 were observed. After the constrictive responses reached equilibrium, U-46619 was added again cumulatively 5 minutes after pre-treatment with a test substance to induce constriction. The pA$_2$ values were calculated in accordance with Van Rossum's method. The results are shown below in Table 4.

These results demonstrate the excellent antagonistic effects of compounds of the present invention on the receptors for both mediators LTD$_4$ and TXA$_2$.

TABLE 4

Results of Test Examples 1 and 2

| Compound No. | LTD$_4$ inhibitory effect (pA$_2$) | TXA$_2$ inhibitory effect (pA$_2$) |
|---|---|---|
| 1 | 9.73 | 8.30 |
| 2 | 9.59 | 7.99 |
| 3 | 9.26 | 8.12 |
| 13 | 9.92 | 7.90 |
| 14 | 9.92 | 8.06 |
| 15 | 9.47 | 8.03 |
| 16 | 10.03 | 7.99 |
| 17 | 9.80 | 7.97 |
| 20 | 9.43 | 8.17 |
| 21 | 9.65 | 7.99 |
| 22 | 9.45 | 8.31 |
| 24 | 9.65 | 8.17 |
| 29 | 9.92 | 7.90 |
| 53 | 9.82 | 8.69 |

TABLE 4-continued

Results of Test Examples 1 and 2

| Compound No. | LTD$_4$ inhibitory effect (pA$_2$) | TXA$_2$ inhibitory effect (pA$_2$) |
| --- | --- | --- |
| 54 | 9.71 | 7.90 |
| 55 | 9.82 | 8.78 |
| 71 | 9.12 | 8.40 |
| 72 | 9.58 | 8.05 |
| 91 | 9.05 | 7.73 |

Test Example 3
Antiasthmatic Effects

The antiasthmatic effects were evaluated by the immediate asthmatic responses of passively sensitized guinea pigs. The previous day, the guinea pigs were sensitized by intravenous injections of a 10-fold diluted anti-DNP-ovalbumin guinea pig serum (guinea pig PCA titer; ×1024) on the ears. The day of the test, after pre-treatment with pyrilamine (10 mg/kg i.p.), normal airway resitances were measured with a double flow plethysmograph in accordance with Pennock et al. The test substances (3 mg/kg) in DMSO were dissolved in 50% normal guinea pig serum-saline and intravenously injected from the ear vein 5 minutes before inhalation of the antigen. Immediate asthmatic responses were induced by 3 minutes of inhalational exposure to 1% ovalbumin in saline as the antigen from an ultrasonic neblizer, and the airway resistances were measured 5 minutes (4 to 6 minutes) after the inhalation. The results are expressed by the inhibition rates given by the following expression:

Inhibition rate (%)=(1−(A−B)/(C−D))×100 wherein A: the airway resistance with a test substance after inhalation of the antigen,
B: the airway resistance with a test substance before inhalation of the antigen,
C: the airway resistance with a control after inhalation of the antigen,
D: the airway resistance with a control before inhalation of the antigen.

The results are shown below in Table 5. These results demonstrate the excellent antiasthmatic effects of compounds of the present invention.

TABLE 5

Results of Test Example 3

| Compound No. | Antiasthmatic effect Inhibition rate (%) |
| --- | --- |
| 1 | 53.5 |
| 24 | 40.5 |
| 38 | 59.5 |
| 70 | 54.0 |

[Acute toxicity test]

Compounds Nos. 1, 5 and 29 were administered to ICR mice intravenously in an amount of 100 mg/kg and orally in an amount of 1000 mg/kg, but none of the mice died.

Formulation Examples

Now, formulation examples using compounds of the present invention will be given below. However, the present invention is by no means restricted by these formulations.

Formulation Example 1

Tablets each containing 100 mg of an active ingredient were prepared in accordance with the following formulation.

| (Ingredients) | (mg) |
| --- | --- |
| Compound No. 1 | 100 |
| Lactose | 30 |
| Corn starch | 40 |
| Crystalline cellulose | 15 |
| Methylcellulose | 3 |
| Magnesium stearate | 2 |

Formulation Example 2

A capsule drug was prepared by encapsulating 190 mg of an ingredient mixture containing 100 mg of an active ingredient in accordance with the following formulation.

| (Ingredients) | (mg) |
| --- | --- |
| Compound No. 1 | 100 |
| Lactose | 50 |
| Corn starch | 30 |
| Crystalline cellulose | 8 |
| Magnesium stearate | 2 |

INDUSTRIAL APPLICABILITY

The novel 2-sulfamoylbenzoic acid derivatives represented by general formula (I) of the present invention are both an antagonistic effect on the LTD$_4$ receptor and an antagonistic effect on the TXA2 receptor and show an excellent antiasthmatic effect. Therefore, the compounds of the present invention are useful as anti-allergic agents for treatment and prevention of various allergic diseases such as allergic bronchial asthma.

What is claimed is:

1. A 2-sulfamoylbenzoic acid derivative represented by general formula (I):

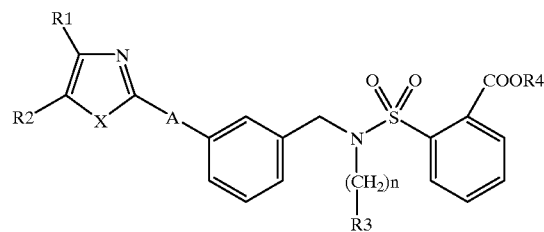

wherein R1 and R2 which may be the same or different, are hydrogen atoms, C$_{3-8}$ cycloalkyl groups, optionally substituted C$_{1-6}$ alkyl groups, optionally substituted aryl groups or form, together with the ring

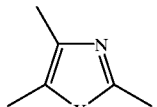

a condensed ring represented by formula

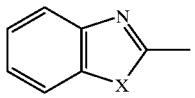

which may be substituted with an optionally substituted $C_{1-6}$ alkyl group, an amino group, a cyano group, a nitro group, a hydroxyl group, a halogen atom or a $C_{1-5}$ alkoxy group, X is an oxygen atom, a nitrogen atom, a sulfur atom or —CH=CH—, R3 is an optionally substituted phenylsulfonylamino group, an optionally substituted phenylsulfonyl group or an optionally substituted phenylsulfoxide group, R4 is a hydrogen atom or an ester residue, n is an integer of from 2 to 6, A is —O—B—, —B—O—, —S—B—, —B—S— or —B—, and B is a $C_{1-6}$ alkylene group or a $C_{2-5}$ alkenylene group, provided that the cases wherein R1 is a $C_{1-6}$ alkyl group, a $C_{3-8}$ cycloalkyl group or a phenyl group, R2 is a hydrogen atom, A is a vinylene group, and X is a sulfur atom are excluded) or a pharmaceutically acceptable salt, hydrate or solvate thereof.

2. The 2-sulfamoylbenzoic acid derivative according to claim 1 or a pharmaceutically acceptable salt, hydrate or solvate thereof, wherein in the general formula (I), X is a sulfur atom, and A is a —CH₂O— or an ethylene group.

3. The 2-sulfamoylbenzoic acid derivative according to claim 2 or a pharmaceutically acceptable salt, hydrate or solvate thereof, wherein in the general formula (I), R1 and R2 which may be the same or different groups and are selected from the group consisting of hydrogen atoms, $C_{3-8}$ cycloalkyl groups, optionally substituted $C_{1-6}$ alkyl groups and optionally substituted aryl groups.

4. A 2-sulfamoylbenzoic acid derivative or a pharmaceutically acceptable salt, hydrate or solvate thereof, selected from the group consisting of 2-{N-[4-(4-chlorobenzenesulfonylamino)butyl]-N-{3-[(4-isopropyl-2-thiazolyl)methoxy]benzyl}}sulfamoylbenzoic acid, 2-{N-[4(4-methylbenzenesulfonylamino)butyl]-N-{3-[(4-isopropyl-2-thiazolyl)methoxy]benzyl}}sulfamoylbenzoic acid, 2-{N-[4-(4-methoxybenzenesulfonylamino)butyl]-N-{3-[(4-isopropyl-2-thiazoyl)methoxy]benzyl}}sulfamoylbenzoic acid, 2-{N-[4-(4-bromobenzenesulfonylamino)butyl]-N-{3-[(4-isopropyl-2-thiazolyl)methoxy]benzyl}}sulfamoylbenzoic acid, 2-{N-[4-(4fluorobenzenesulfonylamino)butyl]-N-{3-[(4-isopropyl-2-thiazolyl)methoxy]benzyl}}sulfamoylbenzoic acid, 2-{N-[4-(4-chlorobenzenesulfonylamino)butyl]-N-{3-[(4-cyclobutyl-2-thiazolyl)methoxy]benzyl}}sulfamoylbenzoic acid, 2-{N-[4-(4-bromobenzenesulfonylamino)butyl]-N-{3-[(4-cyclobutyl-2-thiazolyl)methoxy]benzyl}}sulfamoylbenzoic acid, 2-{N-[4-(4-fluorobenzenesulfonylamino)butyl]-N-{3-[(4-cyclobutyl-2-thiazolyl)methoxy]benzyl}}sulfamoylbenzoic acid, 2-{N-[4-(benzenesulfonylamino)butyl]-N-{3-[(4-cyclobutyl-2-thiazolyl)methoxy]benzyl}}sulfamoylbenzoic acid, 2-{N-[4-(4-methylbenzenesulfonylamino)butyl]-N-{3-[(4-cyclobutyl-2-thiazoyl)methyl]bezyl}}sulfamoylbenzoic acid, 2-{N-[-(4-methoxybenzensulfonylamino)butyl]-N-{3-[(4-cyclobutyl-2-thiazolyl)methoxy]benzyl}}sulfamoylbenzoic acid, 2-{N-[4(4-chlorobenzenesulfonylamino)butyl]-N-{3-[2-(4-cyclopropyl-2-thiazolyl)methoxy]benzyl}}sulfamoylbenzoic acid, 2-{N-[5-(4-chlorobenzenesulfonylamino)pentyl]-N-{3-[2-(4-cyclobutyl-2-thiazolyl)methoxy]benzyl}}sulfamoylbenzoic acid, 2-{N-[5-(4-chlorobenzenesulfonylamino)pentyl]-N-{3-[(4-isopropyl-2-thiazolyl)methoxy]benzyl}}sulfamoylbenzoic acid, 2-{N-[4-(4-chlorobenzenesulfonylamino)butyl]-N-{3-[2-(4-cyclobutyl-2-thiazolyl)ethyl]benzyl}}sulfamoylbenzoic acid, 2-{N-[4-(4-fluorobenzenesulfonylamino)butyl]-N-{3-[2-(4-cyclobutyl-2-thiazolyl)ethyl]benzyl}}sulfamoylbenzoic acid, and 2-{N-4-(4-bromobenzenesulfonylamino)butyl]-N-{3-[2-(4-cyclobutyl-2-thiazolyl)ethyl]benzyl}}sulfamoylbenzoic acid.

5. The 2-sulfamoylbenzoic acid derivative according to claim 1 or a pharmaceutically acceptable salt, hydrate or solvate thereof, wherein in the general formula (I), X is —CH=CH—, and A is selected from the group consisting of —CH₂O—, an ethylene group, and a vinylene group.

6. The 2-sulfamoylbenzoic acid derivative according to claim 1 or a pharmaceutically accepabe salt, hydrate or solvate thereof, wherein in the general formula (I), R1 and R2 form together with the ring

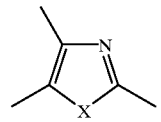

a condensed ring represented by formula

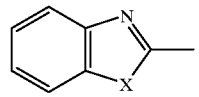

which may be substituted with a group selected from an optionally substituted $C_{1-6}$ alkyl group, an amino group, a cyano group, a nitro group, a hydroxyl group, a halogen atom, and $C_{1-5}$ alkoxy group.

7. A 2-sulfamoylbenzoic acid derivative or a pharmaceutcally acceptable salt, hydrate or solvate thereof selected from the group consisting of 2-{N-[4-(4-chlorobenzenesulfonylamino)butyl]-N-{3-[2-(2-guinolyl)ethyl]benzyl}}sulfamoylbenzoic acid, 2-{N-[4-(4-bromobenzenesulfonylamino)butyl]-N-{3-[2-(2-guinolyl)ethyl]benzyl}}sulfamoylbenzoic acid, 2-{N-[4-(4-fluorobenzenesulfonylamino)butyl]-N-{3-[2-(2-guinolyl)ethyl]benzyl}}sulfamoylbenzoic acid, 2-{N-[4-(4-methylbenzenesulfonylamino)butyl]-N-{3-2-(2-guinolyl)ethyl]benzyl}}sulfamoylbenzoic acid, 2-{N-[4-(4-methoxybenenesulfonylamino)butyl]-N-{3-[2-(2-guinolyl)ethyl]benzyl}}sulfamoylbenzoic acid, 2-{N[4-benzenesulfonylamino)butyl]-N-{3-[2-(2-guinolyl)ethyl]benzyl}}sulfamoylbenzoic acid, 2-{N-[4-(4-chlorobenzenesulfonylamino)butyl]-N-{3-[2-(7-chloro-2-guinolyl)ethyl]benzyl}}sulfamoylbenzoic acid, 2-{N-[4-(4-bromobenzenesulfonylamino)butyl]-N-{3-[2-(7-chloro-2-guinolyl)ethyl]benzyl}}sulfamoylbenzoic acid, 2-{N-[4-(4-fluorobenzenesulfonylamino)butyl]-N-{3-[2-(7-chloro-2-guinolyl)ethyl]benzyl}}sulfamoylbenzoic acid, 2-{N-[4-(4-methylbenzenesulfonylamino)butyl]-N-{3-[2-(7-chloro-2-guinolyl)ethyl]benzyl}}sulfamoylbenzoic acid, 2-{N-[4-(4-methoxybenzenesulfonylamino)butyl]-N-{3-[2-(7-chloro-2-guinolyl)ethyl]benzyl}}sulfamoylbenzoic acid, 2-{N-[4-(benzenesulfonylamino)butyl]-N-{3-[2-(7-chloro-2-guinolyl)ethyl]benzyl}}sulfamoylbenzoic acid, 2-{N-[5-(4-chlorobenzenesulfonylamino)pentyl]-N-{3-[2-(7-chloro-2-guinolyl)ethyl]benzyl}}sulfamoylbenzoic acid, 2-{N-[5-(4-chlorobenzenesulfonylamino)pentyl]-N-{3-[2(2-guinolyl)ethyl]benzyl}}sulfamoylbenzoic acid, 2-{N-[4-(4-chlorobenzenesulfonylamino)butyl]-N-{3-[(2-guinolyl)methoxy]benzyl}}sulfamoylbenzoic acid, 2-{N-[4-(4-chlorobenzenesulfonylamino)butyl]-N-{3-[(7-chloro-2-quinolyl)methoxy]benzyl}}sulfamoylbenzoic acid, 2-{N-[4-(4- chlorobenzenesulfonylamino)butyl]-N-{3-[2-(2-quinolyl)ethenyl]bensyl}}sulfamoylbenzoic acid, and 2-{N-[4-(4- chlorobenzenesulfonylamino)butyl]-N-{3-[(7-chloro-2-quinoyl)ethenyl]benzyl}}sulfamoylbenzoic acid.

8. A sulfamoylbenzoic acid derivative or a pharmaceutically acceptable salt, hydrate or solvate thereof selected form the group consisting of 2-{N-[4(4-chlorobenzenesulfonylamino)butyl]-N-{3-[(4-isopropyl-2-thiazolyl)metboxy]benzyl}}sulfamoylbenzoic acid, 2-{N-[5-(4-chlorobenzenesulfonylamino)pentyl]-N-{3-[(4-isopropyl-2-thiazolyl)methoxy]benzyl}}sulfamoylbenzoic acid, 2-{N-[4-(4-chlorobenzenesulfonylamino)butyl]-N-{3-[2-(4-cyclobutyl-2-thiazolyl)ethyl]benzyl}}sulfamoylbenzoic acid, and 2-{N-[5-(4-chlorobenzenesulfonylamino)pentyl]-N-{3-[2-(7-chloro-2-quinolyl)ethyl]benzyl}}sulfamoylbenzoic acid, and 2-{N-[5-(4-chlorobenzenesulfonylamino)pentyl]-N-{3-[2-(2-quinolyl)ehtyl]benzyl}}sulfamoylbenzoic acid.

9. A benzylamine derivative represented by a general formula (II):

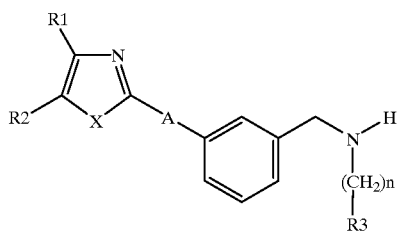

wherein R1 and R2 which may be the same or different, are hydrogen atoms, $C_{3-8}$ cycloalkyl groups, optionally substituted $C_{1-6}$ alkyl groups, optionally substituted aryl groups or form, together with the ring

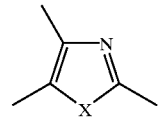

a condensed ring represented by formula

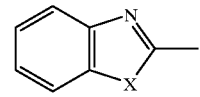

which may be substituted with an optionally substituted $C_{1-6}$ alkyl group, an amino acid group, a cyano group, a nitro group, a hydroxyl group, a halogen atom or a $C_{1-5}$ alkoxy group, X is an oxygen atom, a nitrogen atom, a sulfur atom or —CH=CH—, R3 is an optionally substituted phenylsulfonylamino group, an optionally subtiiuted phenylsulfonyl group or an optionally substituted phenylsulfoxide group, n is an integer of from 2 to 6, A is —O—B—, —B—O—, —S—B—, —B—S— or —B—, and B is a $C_{1-6}$ alkylene group or a $C_{2-5}$ alkenylene group, provided that the cases wherein R1 is a $C_{1-6}$ alkyl group, a $C_{3-8}$ cycloalkyl group or a phenyl group, R2 is a hydrogen atom, A is a vinylene group, and X is a sulfur atom are excluded) or a pharmaceutically acceptable salt thereof.

10. A pharmaceutical composition comprising as an active ingredient the 2-sulfamoylbenzoic acid derivative according to claim 1 or a pharnaceutically acceptable salt, hydrate or solvate thereof and a pharmaceutically acceptable carrier.

11. An anti-allergic agent comprising as an active ingredient the 2-sulfamoylbenzoic acid derivative according to claim 1 or a pharmaceutically acccptable salt, hydrate or solvate thereof and a pharmaceutically acceptable carrier.

12. A leucotriene and thromboxane $A_2$ antagonistic agent comprising as an active ingredient the 2-sulfamoylbenzoic acid derivative according to claim 1 or a pharmaceutically acceptable salt, hydrate or solvate thereof and a pharmaceutically acceptable carrier.

13. The pharmaceutical composition of claim 10 wherein the solvate is formed by using a solution selected from the group consisting of acetone, 2-butanol, 2-propanol, ethanol, ethyl acetate, tetrahydrofuran and diethyl ether.

14. The anti-allergic agent of claim 11 wherein the solvate is formed by using a soluton selected from the group consisting of acetone, 2-butanol, 2-propanol, ethanol, ethyl acetate, tetrahydrofuran and diethyl ether.

15. The leucotriene and thromboxane $A_2$ antagonistic agent of claim 12 wherein the solvate is formed by using a solution selected from the group consisting of acetone, 2-butanol, 2-propanol, ethanol, ethyl acetate, tetrahydrofuran and diethyl ether.

* * * * *